(12) United States Patent
Huang et al.

(10) Patent No.: US 7,939,067 B2
(45) Date of Patent: May 10, 2011

(54) PURIFIED RECOMBINANT BATROXOBIN WITH HIGH SPECIFIC ACTIVITY

(75) Inventors: Xiudong Huang, Shanghai (CN); Peixin Chen, Shanghai (CN); Xuegong Pan, Shanghai (CN); Qiang Wang, Shanghai (CH); Zhifang Cao, Shanghai (CN)

(73) Assignee: Shanghai Wanxing Biopharmaceuticals, Co., Ltd., Shanghai (CN)

( * ) Notice: Subject to any disclaimer, the term of this patent is extended or adjusted under 35 U.S.C. 154(b) by 0 days.

(21) Appl. No.: 12/568,234

(22) Filed: Sep. 28, 2009

(65) Prior Publication Data

US 2010/0047229 A1     Feb. 25, 2010

Related U.S. Application Data

(63) Continuation of application No. PCT/CN2007/001036, filed on Mar. 30, 2007.

(51) Int. Cl.
 *A61K 38/48* (2006.01)
 *C12N 9/50* (2006.01)

(52) U.S. Cl. ...................... 424/94.64; 435/219

(58) Field of Classification Search ............... 424/94.64; 435/219
See application file for complete search history.

(56) References Cited

U.S. PATENT DOCUMENTS

| | | | |
|---|---|---|---|
| 3,849,252 A | 11/1974 | Percs et al. | |
| 5,595,974 A | 1/1997 | Tomaru | |
| 5,869,044 A | 2/1999 | Tomaru et al. | |
| 6,016,830 A | 1/2000 | Niakan et al. | |
| 6,399,576 B1 | 6/2002 | Li | |
| 6,416,717 B1 | 7/2002 | Suzuki et al. | |
| 2006/0281147 A1 | 12/2006 | You et al. | |

FOREIGN PATENT DOCUMENTS

| | | |
|---|---|---|
| CN | 1370833 A | 9/2002 |
| CN | 1534093 A | 10/2004 |
| CN | 1727002 A | 2/2006 |
| EP | 0 719 791 A2 | 7/1996 |
| EP | 0 750 912 A2 | 1/1997 |
| EP | 0 826 374 A2 | 3/1998 |
| EP | 0 984 279 A2 | 3/2000 |
| JP | 63-49084 A | 3/1988 |
| JP | 2-124092 A | 5/1990 |

OTHER PUBLICATIONS

Tang et al. [Thrombosis Research vol. 124, Issue 5, Nov. 2009, pp. 631-639.*
Itoh N et al. [The Journal of biological chemistry, (Mar. 5, 1987) vol. 262, No. 7, pp. 3132-3135].*
International Search Report of PCT/CN2007/001036, dated Jan. 3, 2008.
You et al. "Functional Characterization of recombinant batroxobin, a snake venom thrombin-like enzyme, expressed from *Pichia pastoris*." FEBS Letters, 571, 2004, pp. 67-73.

* cited by examiner

*Primary Examiner* — Tekchand Saidha
(74) *Attorney, Agent, or Firm* — Hamre, Schumann, Mueller & Larson, P.C.

(57) ABSTRACT

A purified recombinant batroxobin with high specific activity, which has the following properties: (a) the batroxobin has a molecular weight of 29-32 kDa; (b) at least 90% of the batroxobin have 6 pairs of disulfide bonds which correctly match at $Cys^7$-$Cys^{139}$, $Cys^{26}$-$Cys^{42}$, $Cys^{74}$-$Cys^{230}$, $Cys^{118}$-$Cys^{184}$, $Cys^{150}$-$Cys^{163}$ and $Cysl^{174}$-$Cys^{199}$; (c) positions 146 and 225 in SEQ ID NO:1 are modified as N-glycosylation; and (d) the specific activity of the batroxobin is equal to or greater than 1500 KU/mg protein.

9 Claims, 28 Drawing Sheets

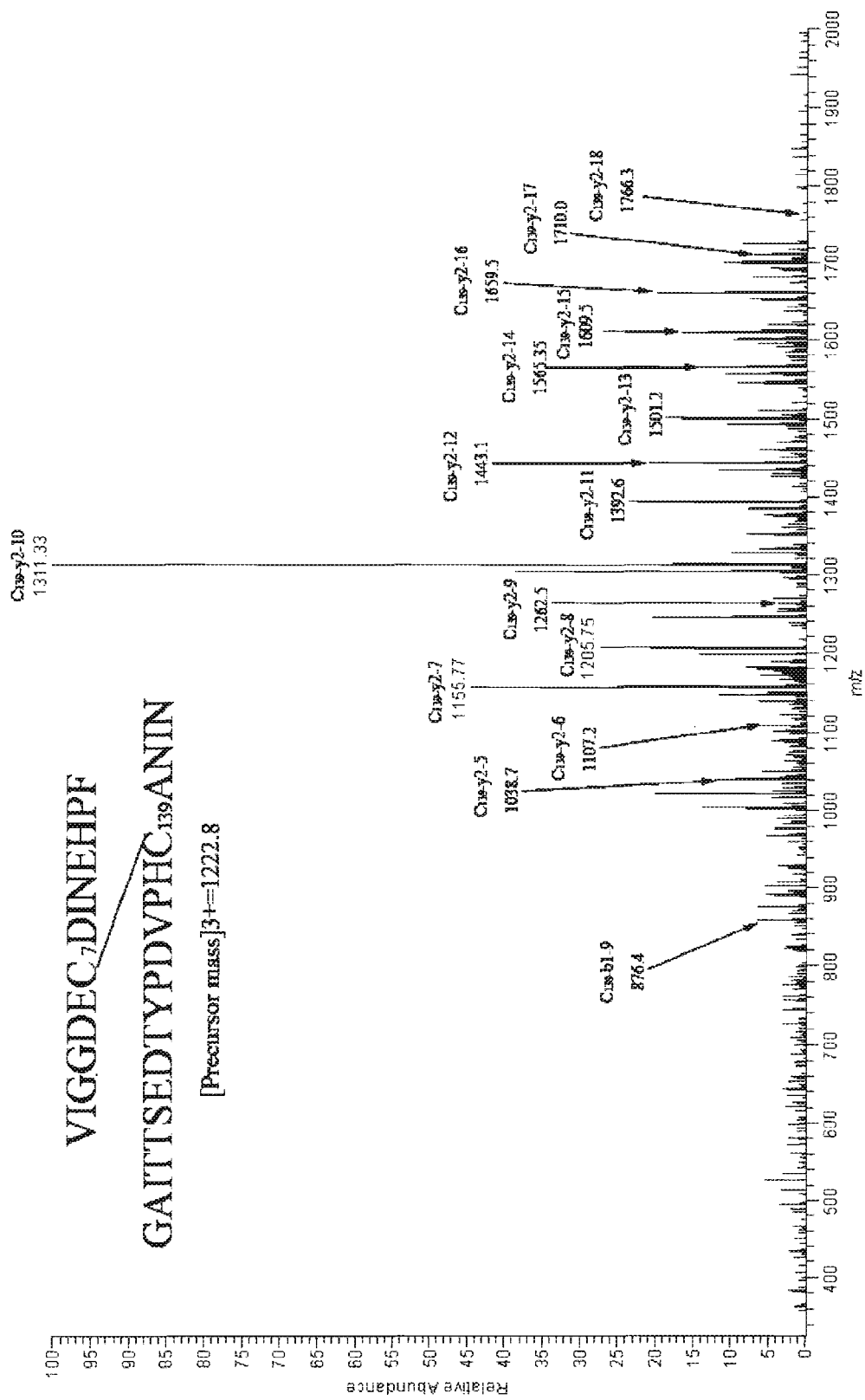

Fig 9B

1 VIGGDECDIN EHPFLAFMYY SPRYFCGMTL INQEWVLTAA HCNRRFMRIH

51 LGKHAGSVAN YDEVVRYPKE KFICPNKKKN VITDKDIMLI RLDRPVKNSE

101 HIAPLSLPSN PPSVGSVCRI MGWGAITTSE DTYPDVPHCA NINLFNNTVC

151 REAYNGLPAK TLCAGVLQGG IDTCGGDSGG PLICNGQFGG ILSWGSDPCA

201 EPRKPAFYTK VFDYLPWIQS IIAGNKTATC P    (SEQ ID NO:1)

PURIFIED RECOMBINANT BATROXOBIN WITH HIGH SPECIFIC ACTIVITY

TECHNICAL FIELD

The invention relates to the genetic engineering field and, in particular, to a purified recombinant batroxobin with high specific activity and the use thereof.

TECHNICAL BACKGROUND

Long before 1936, Van Klobusitzky et al., the scholars of Austria, purified and refined an enzymatic haemostatic, batroxobin, from the venom of Bothrops atrox. The initial translation of the batroxobin in China was "baqimei". Batroxobin belongs to the serine proteases family. Its physiological function and molecular size are similar to those of thrombin. Therefore, it was called as "xueningmei" later. However, people at home and broad defined batroxobin with different meanings in different periods along with the development of research. There are five subspecies for Brazilian lancehead snake (Bothrops atrox). The batroxobin obtained from certain subspecies exhibits the hemostatic efficacy. The batroxobin obtained from other subspecies, however, exhibits the function of removing fibrinogen. As a result, the difference in the species of snake results in that the proteins generally called as "baqimei" in fact exhibit completely different biological and chemical essence. Some of them possess hemostatic efficacy as their main function, while the other possess the degradation of fibrinogen as their main function. Further investigation and research are needed to determine whether or not said difference in chemical essence is derived from the difference in the amino acid sequence or from the different in the protein modification, such as glycoconjugates and the like.

Currently, there are some patents (U.S. Pat. Nos. 5,595,974, 5,869,044, 6,106,830, 6,399,576, 6,416,717; Eur. Pat. Nos: 0984279, 0826374, 0750912, 0719791) and investigation reports relating to the use of batroxobin that is extracted and prepared only from the snake venom in treating many clinical indications, such as myocardial infarction, senile dementia, stroke, sudden deafness and the like. No researches are reported about the animal tests and clinical investigation of the recombinant batroxobin. The batroxobin biologically extracted from the snake venom is mainly obtained from the venom of Bothrops moojeni, Bothrops atrox. However, the content is low and it is difficult to obtain the starting material and the purified natural batroxobin. Generally, there are a few of snake toxins and many unknown impurities retained in the final product. This raises the potential risk for clinical use. The theoretical molecular weight of the highly purified natural batroxobin should also be 25.6 kDa. However, in fact, the actual molecular weight are 37-43 kDa because the protein has experienced a glycosylation modification when it is secreted and expressed in the cells of poison gland of the viper. The alteration of molecular weight may result from the degree of glycosylation modification or the loss of the sugar chain due to different purification processes, and the like. Since the source of the starting material, i.e., the snake venom, is influenced by the scale of the cultivated snakes and the change of four seasons, it is difficult to control the quality of natural batroxobin extracted and prepared from the snake venom and the specific activity thereof is very unstable.

The molecular biology study on batroxobin, a protein obtained from the snake venom, advanced slowly until in 1987 and 1988, the investigators in Japan finished the sequencing work for the cDNA and genomic DNA of batroxobin gene. In 1991, the investigators in Fujisawa Pharmaceutical (Japan) used a fusion expression system in E. coli to express the component as inclusion body via the gene recombinant method. And then they obtained batroxobin, which they claimed had a biological activity, by electrophoresis and cleaving the fusion protein with thrombin and they filed an patent application (Pat. No. JP2124092, 1990). It is always technically difficult to produce the protein enriched in disulfide bonds via the genetic engineering means, especially for the serine proteolytic enzymes containing many pairs of disulfide bond. This is because the disulfide bonds may mismatch in high rate and the products obtained in prokaryotic expression system are almost in the form of inclusion bodies. Although the Fujisawa Pharmaceutical Co., Ltd in Japan reported that the target protein having activity could be obtained via denaturing and re-naturing the inclusion body, the specific activity of the protein is low and the reproducibility is poor. And until now it is not found that the recombinant batroxobin product of that company has been produced and marketed.

Therefore, there still is an urgent need in the art to provide a recombinant batroxobin product with high activity, the production of which is not limited by the seasons or the production scale is readily controlled, and which has a high rate in the correct matching of the disulfide bond.

SUMMARY OF INVENTION

The first purpose of the invention is to provide a gene recombinant batroxobin.

The second purpose of the invention is to provide the uses of the gene recombinant batroxobin.

The third purpose of the invention is to provide a pharmaceutical composition containing the gene recombinant batroxobin.

The first aspect of the invention provides a purified recombinant batroxobin, which exhibits the following properties:

(a) the batroxobin has a molecular weight of 29-32 kDa;

(b) 90% of batroxobin have 6 pairs of disulfide bonds which correctly match at $Cys^7$-$Cys^{139}$, $Cys^{26}$-$Cys^{42}$, $Cys^{74}$-$Cys^{230}$, $Cys^{118}$$Cys^{184}$,$Cys^{150}$-$Cys^{163}$ and $Cys^{174}$-$Cys^{199}$;

(c) positions 146 and 225 in SEQ ID NO:1 are modified as N-glycosylation; and (d) the specific activity of the batroxobin is equal to or greater than 1500 KU/mg protein.

In another preferred embodiment, at least 95% of the recombinant batroxobin have 6 pairs of disulfide bonds which correctly match.

In another preferred embodiment, the glycosylation in the batroxobin is N-glycosylation of the asparagine residue (Asn) in the following sites: $Asn^{146}$-$Asn^{147}$-$Thr^{148}$ and $Asn^{225}$-$Lys^{226}$-$Thr^{228}$.

In another preferred embodiment, the N-glycosylation modification adds 4000-6000 Da to the molecular weight of the batroxobin protein on the basis of 25.6 kDa.

In another preferred embodiment, the specific activity of the batroxobin is 1500-3000 KU/mg.

In another preferred embodiment, at least 99% of the batroxobin have 6 pairs of disulfide bonds which correctly match.

The second aspect of the invention is to provide a use of the above purified recombinant batroxobin in the preparation of a hemostatic drug.

The third aspect of the invention is to provide a pharmaceutical composition, which comprises the recombinant batroxobin hereinabove and a pharmaceutically acceptable carrier.

In another preferred embodiment, the composition further comprises a hydrolyzed gelatin as a stabilizer.

In another preferred embodiment, the composition is a liquid or a freeze-dried powder.

The invention hereby provides a recombinant batroxobin product with high activity, the production of which is not limited by the seasons and the production scale can be readily controlled, and which has a high rate in the correct matching of the disulfide bonds.

DESCRIPTION OF DRAWINGS

FIGS. 7A-7D shows the detection pictures of disulfide bond C7-C139, wherein 7A shows the mass charge ratio m/z map of the peptide segment containing disulfide bind C7-C139;

7B shows the MS/MS map of the peptide segment containing disulfide bind C7-C139;

7C shows the MS/MS map of the peptide segment containing cysteine C7;

7D shows the MS/MS map of the peptide segment containing cysteine C139.

Figure 8A:
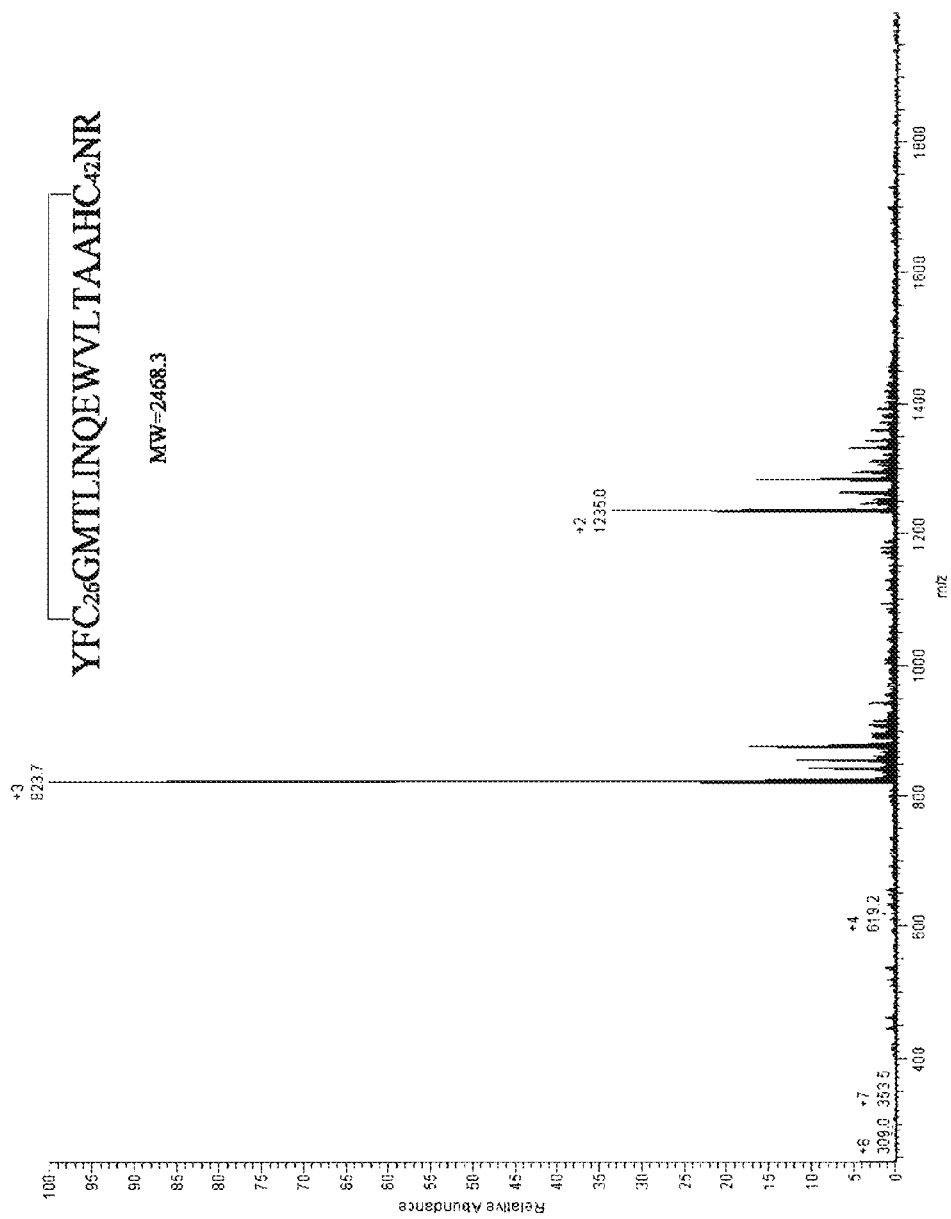
Figure 8B:
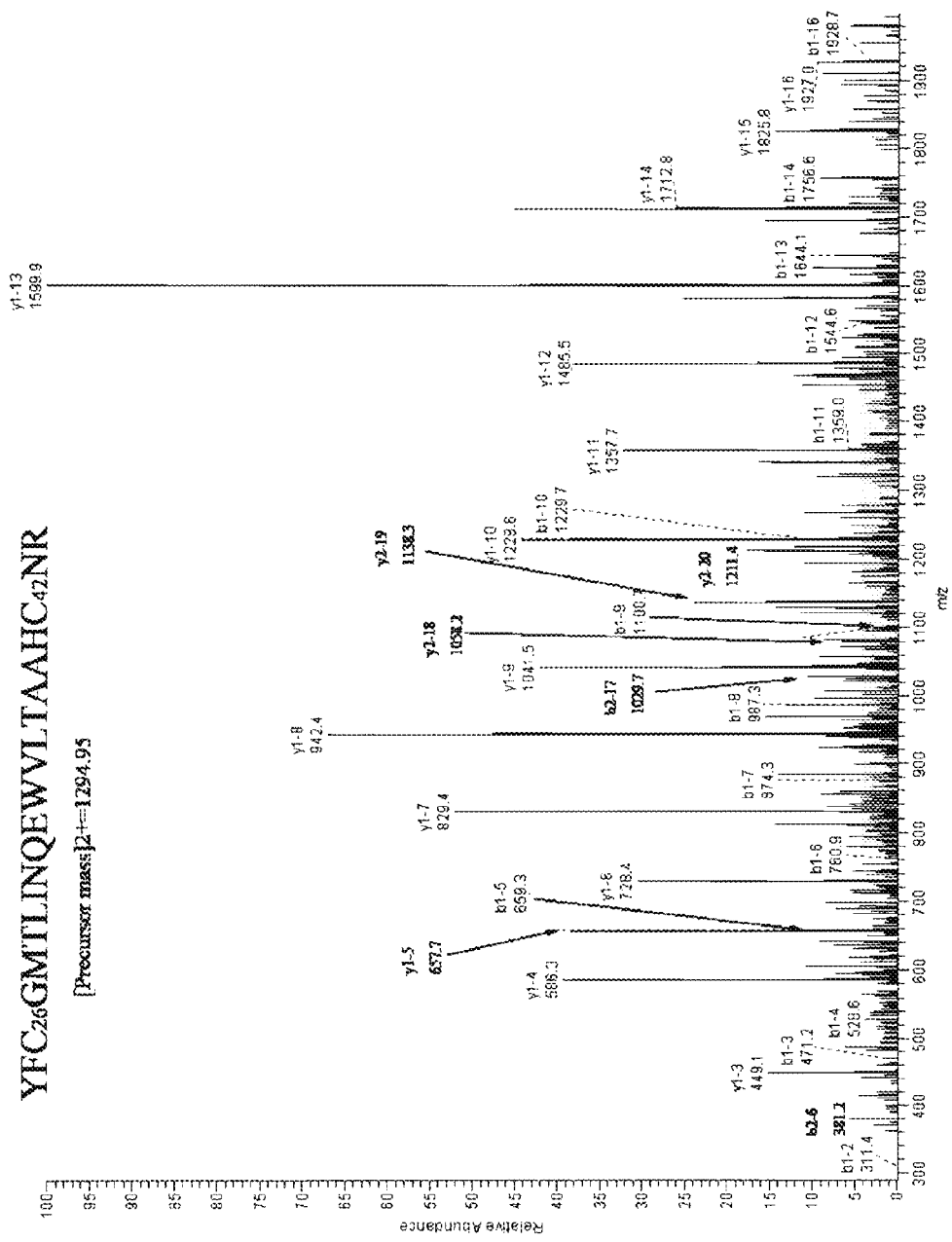
Figure 9A:
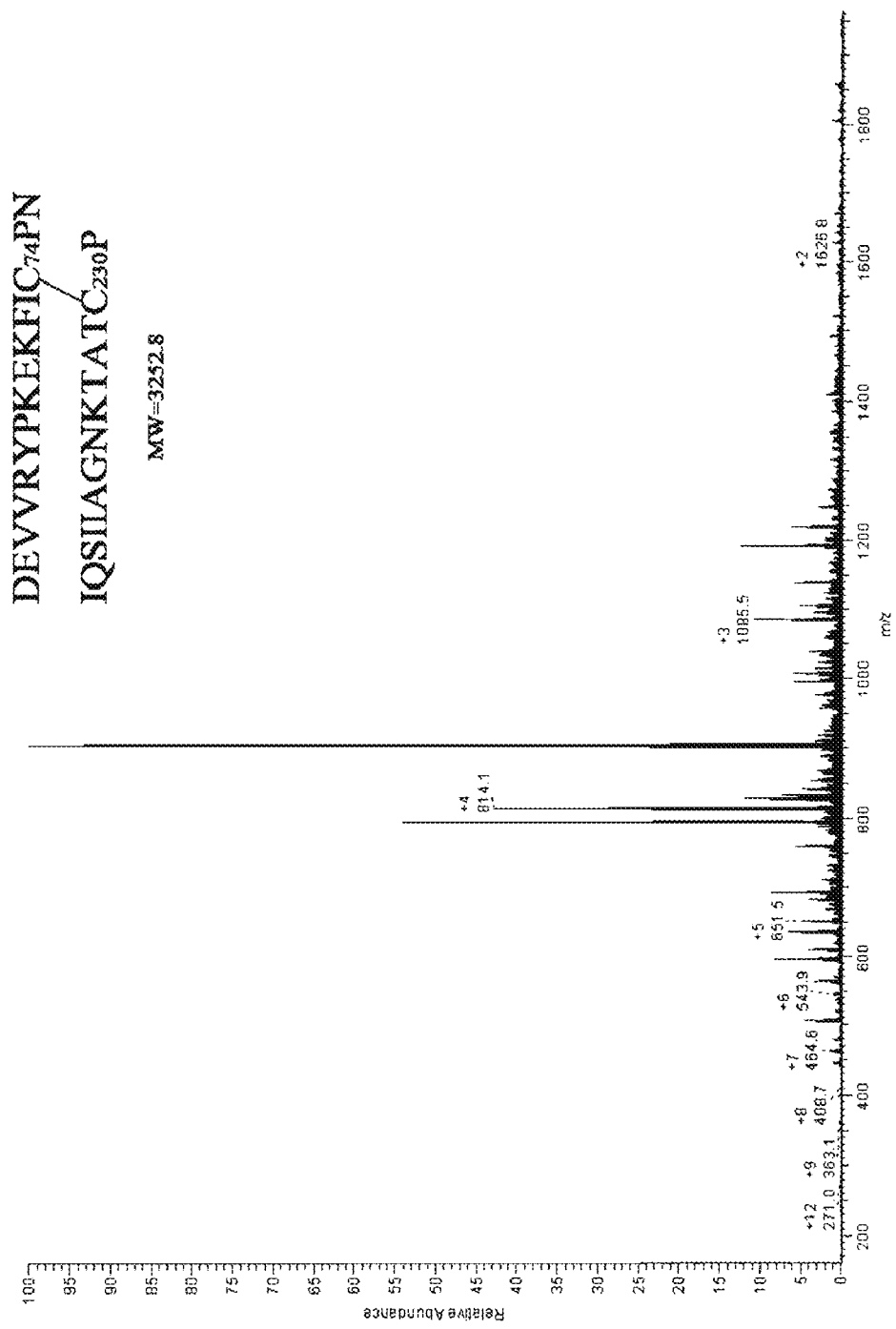
Figure 9C:
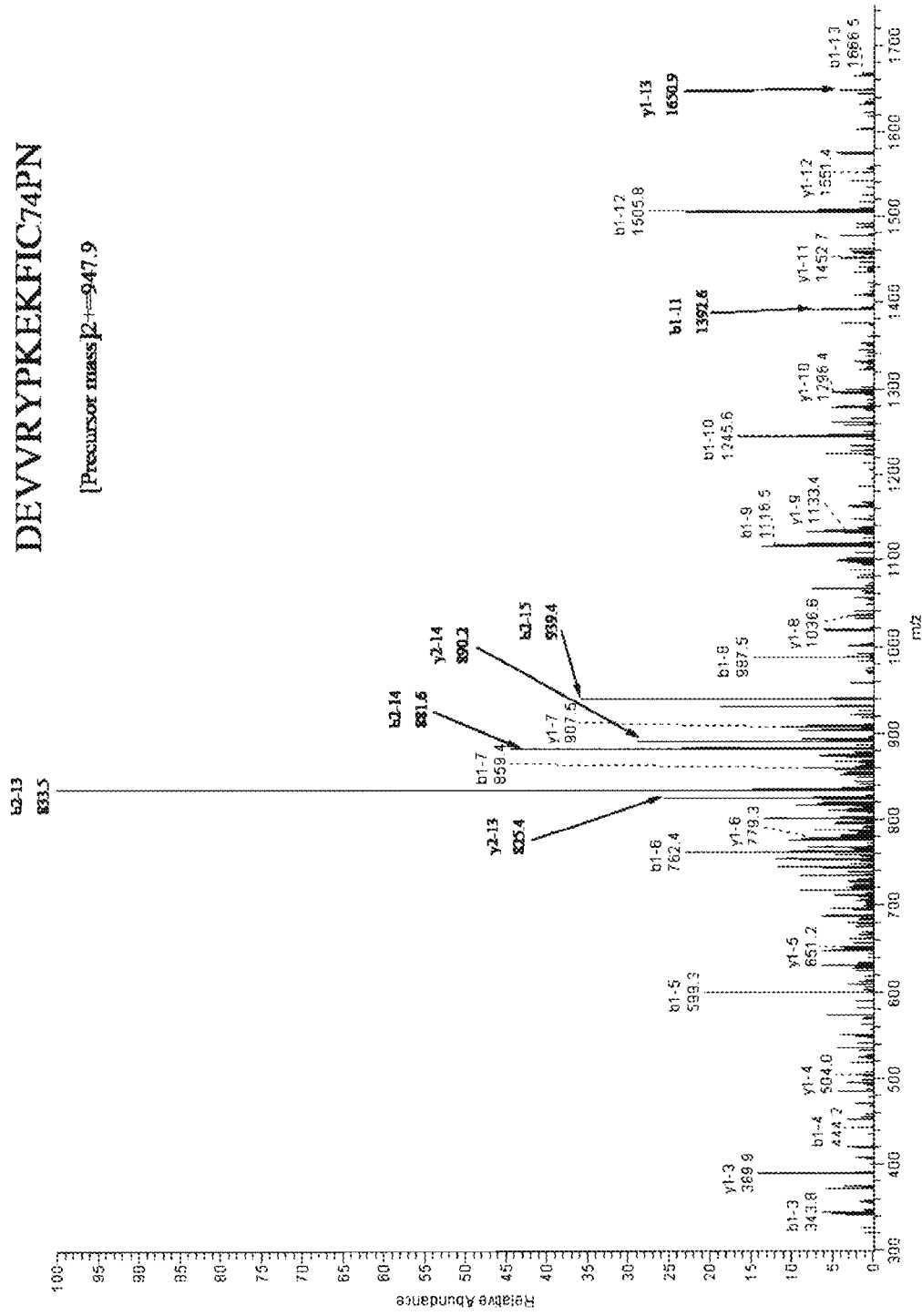
Figure 9D:
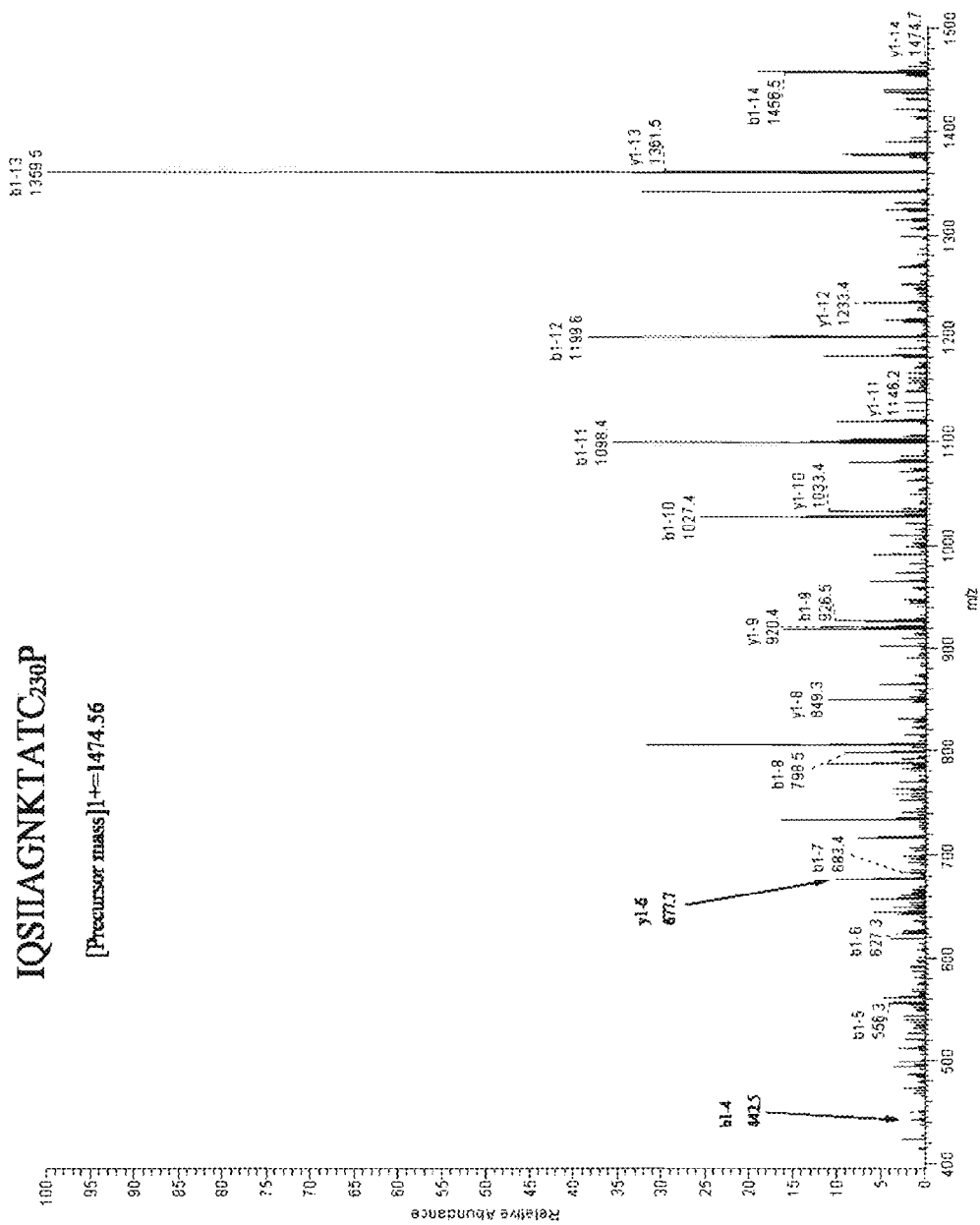

FIGS. 8A-8B shows the detection pictures of disulfide bond C26-C42, wherein 8A shows the mass charge ratio m/z map of the peptide segment containing disulfide bind C26-C42;

8B shows the MS/MS map of the peptide segment containing cysteines C26 and C42.

Figure 9B:
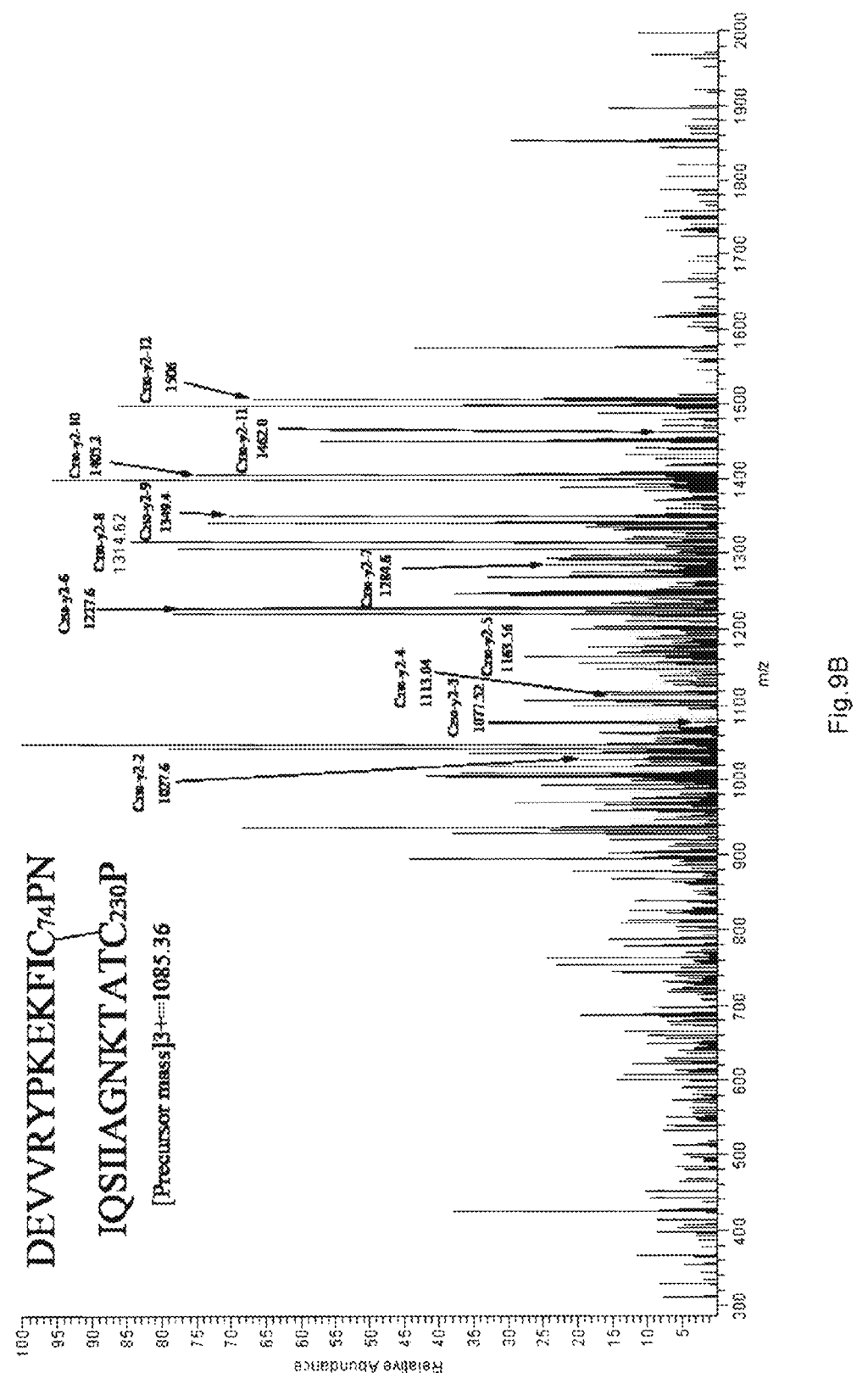

FIGS. 9A-9D shows the detection pictures of disulfide bond C74-C230, wherein 9A shows the mass charge ratio m/z map of the peptide segment containing disulfide bind C74-C230;

9B shows the MS/MS map of the peptide segment containing disulfide bind C74-C230;

9C shows the MS/MS map of the peptide segment containing cysteine C74;

9D shows the MS/MS map of the peptide segment containing cysteine C230.

Figure 10A:
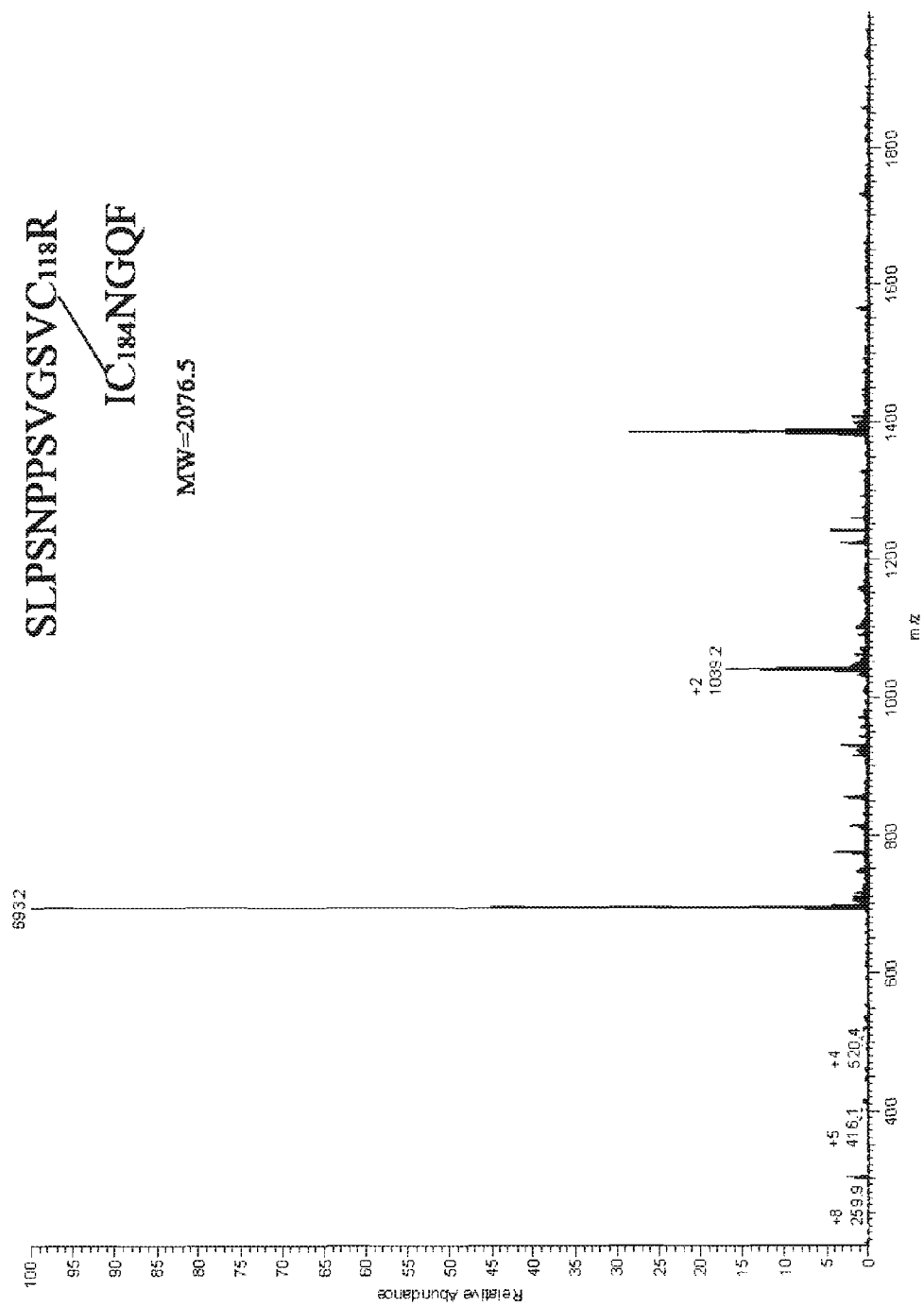
Figure 10B:
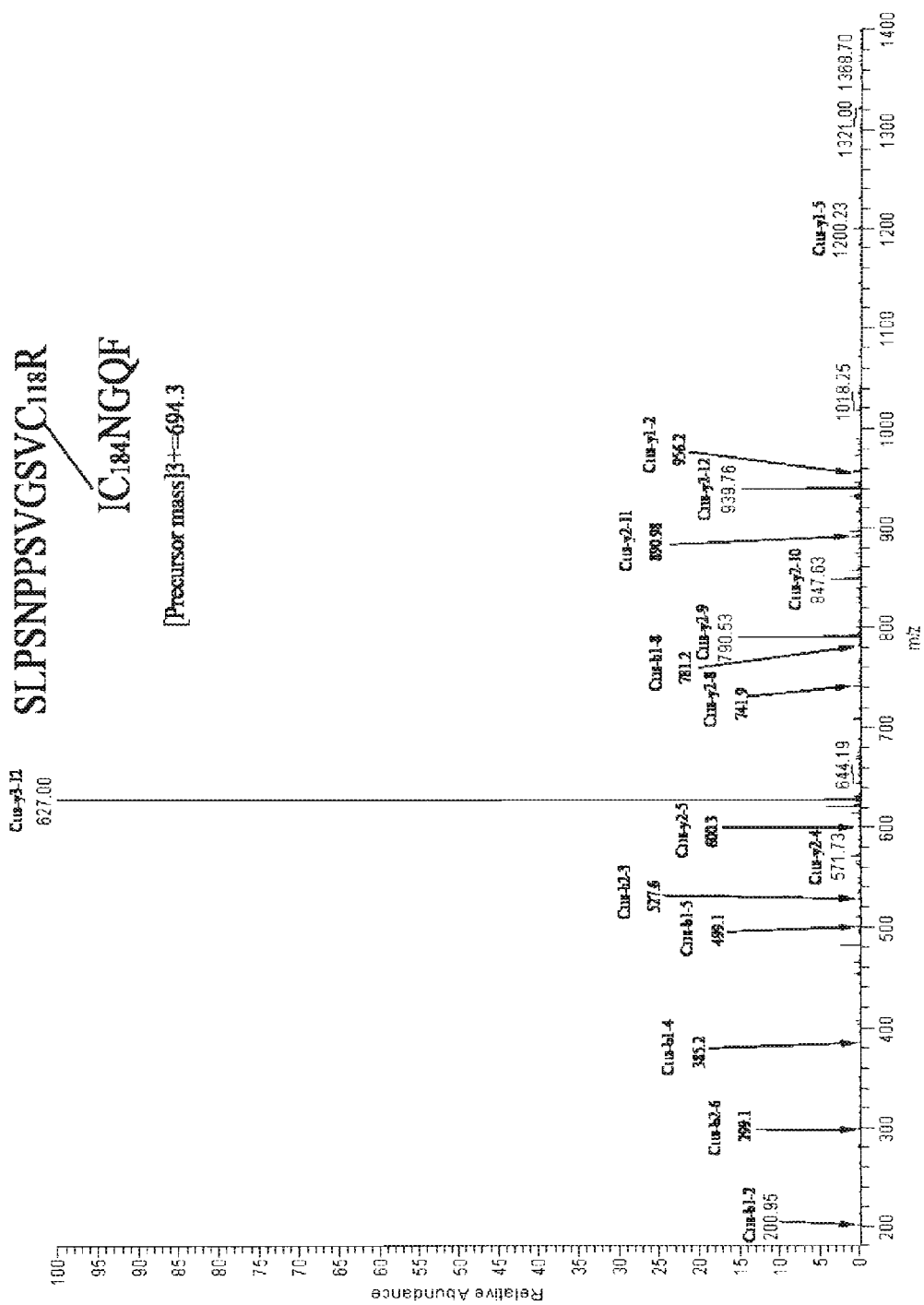
Figure 10C:
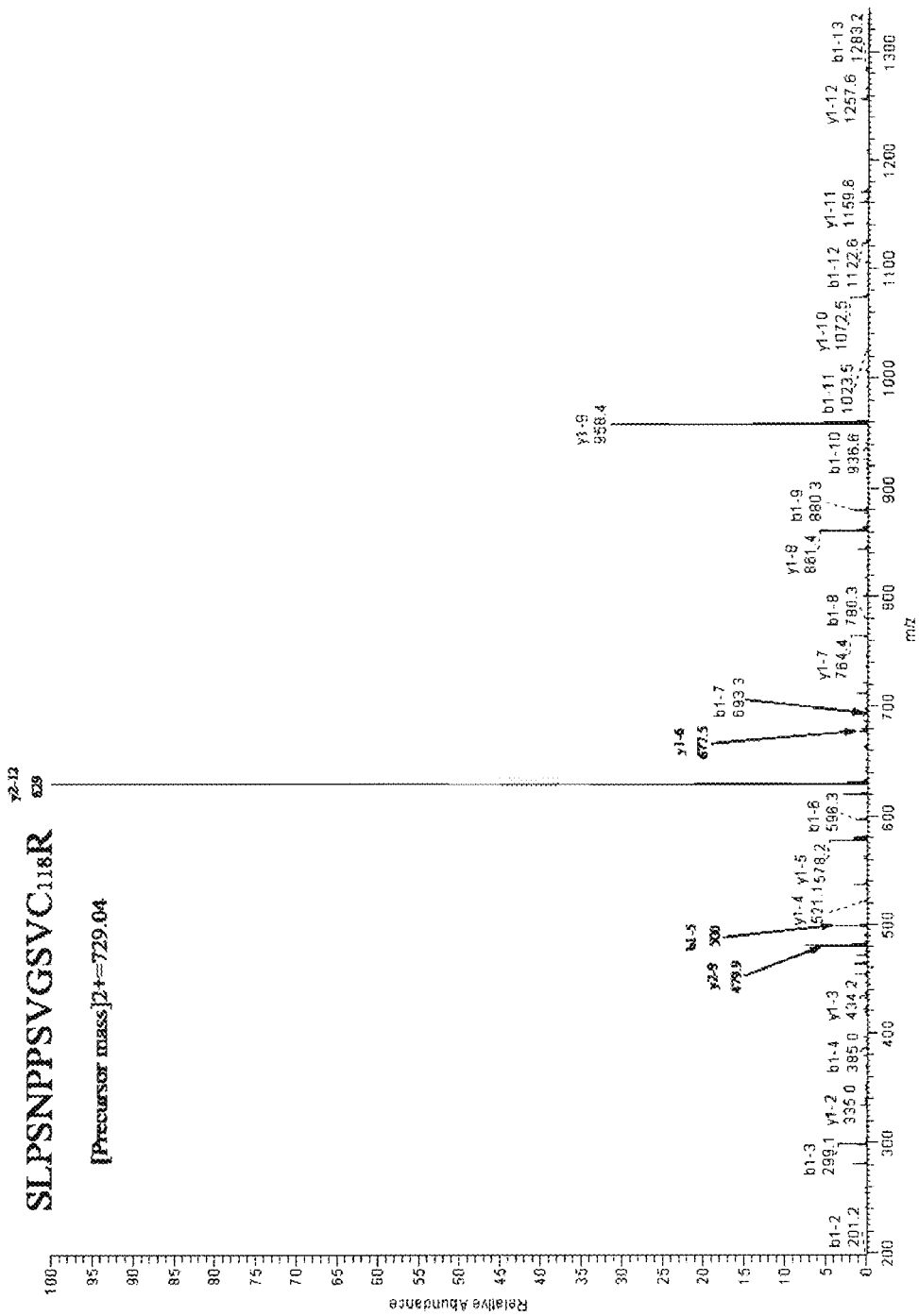

FIGS. 10A-10C shows detection pictures of disulfide bond C118-C184, wherein 10A shows the mass charge ratio m/z map of the peptide segment containing disulfide bind C118-C184;

10B shows the MS/MS map of the peptide segment containing disulfide bind C118-C184, 10C shows the MS/MS map of the peptide segment containing cysteine C118.

Figure 11A:
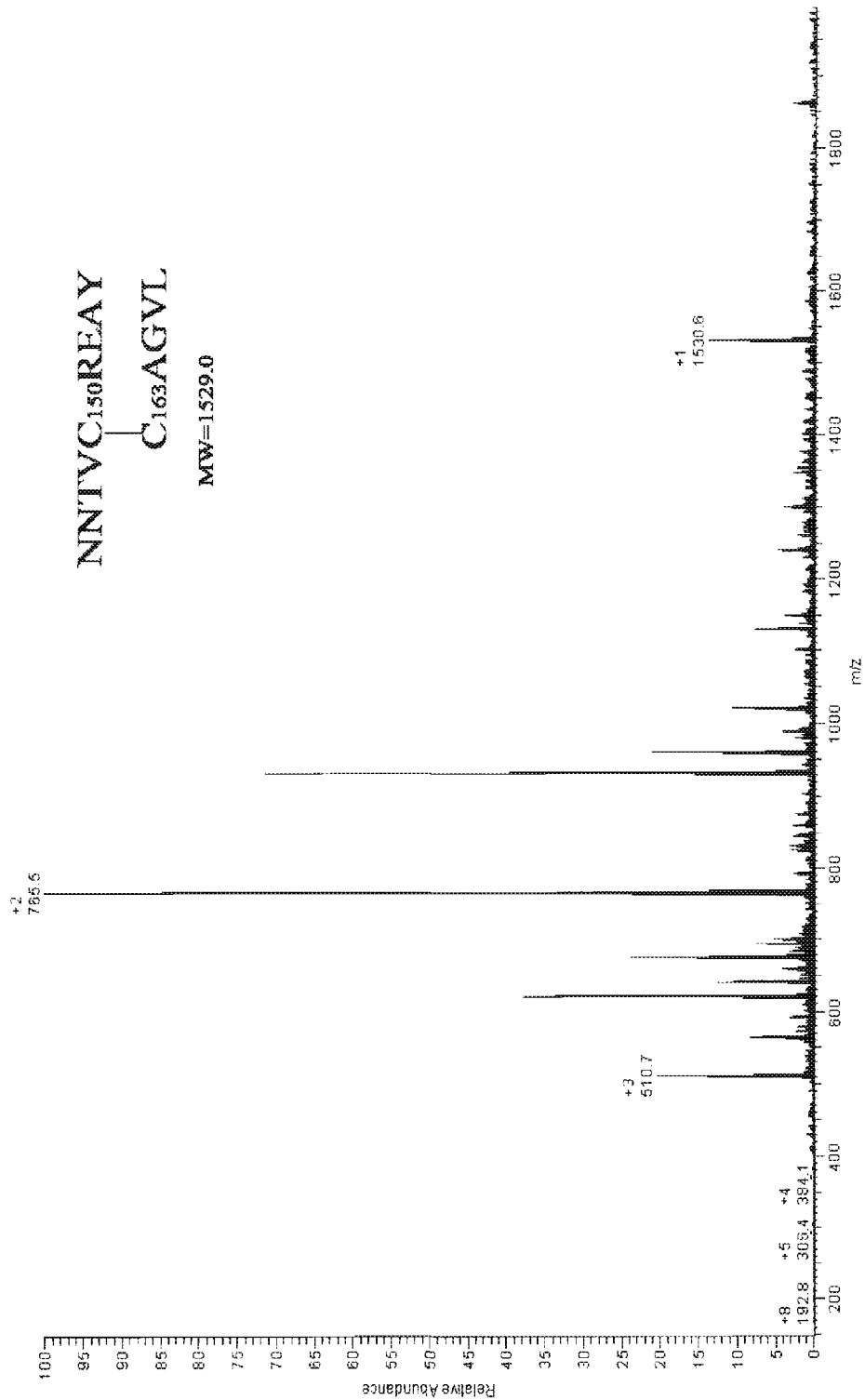
Figure 11B:
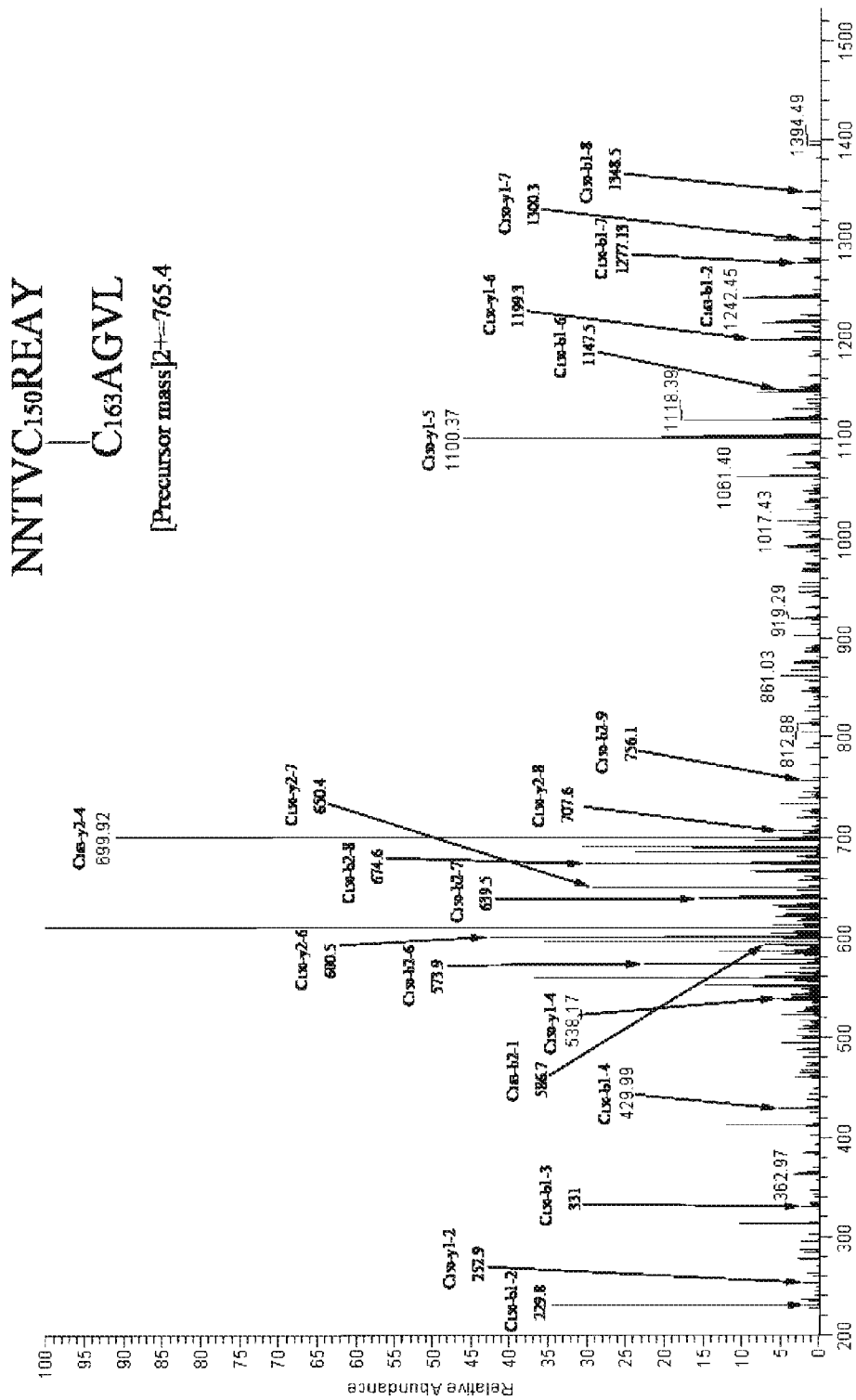
Figure 11C:
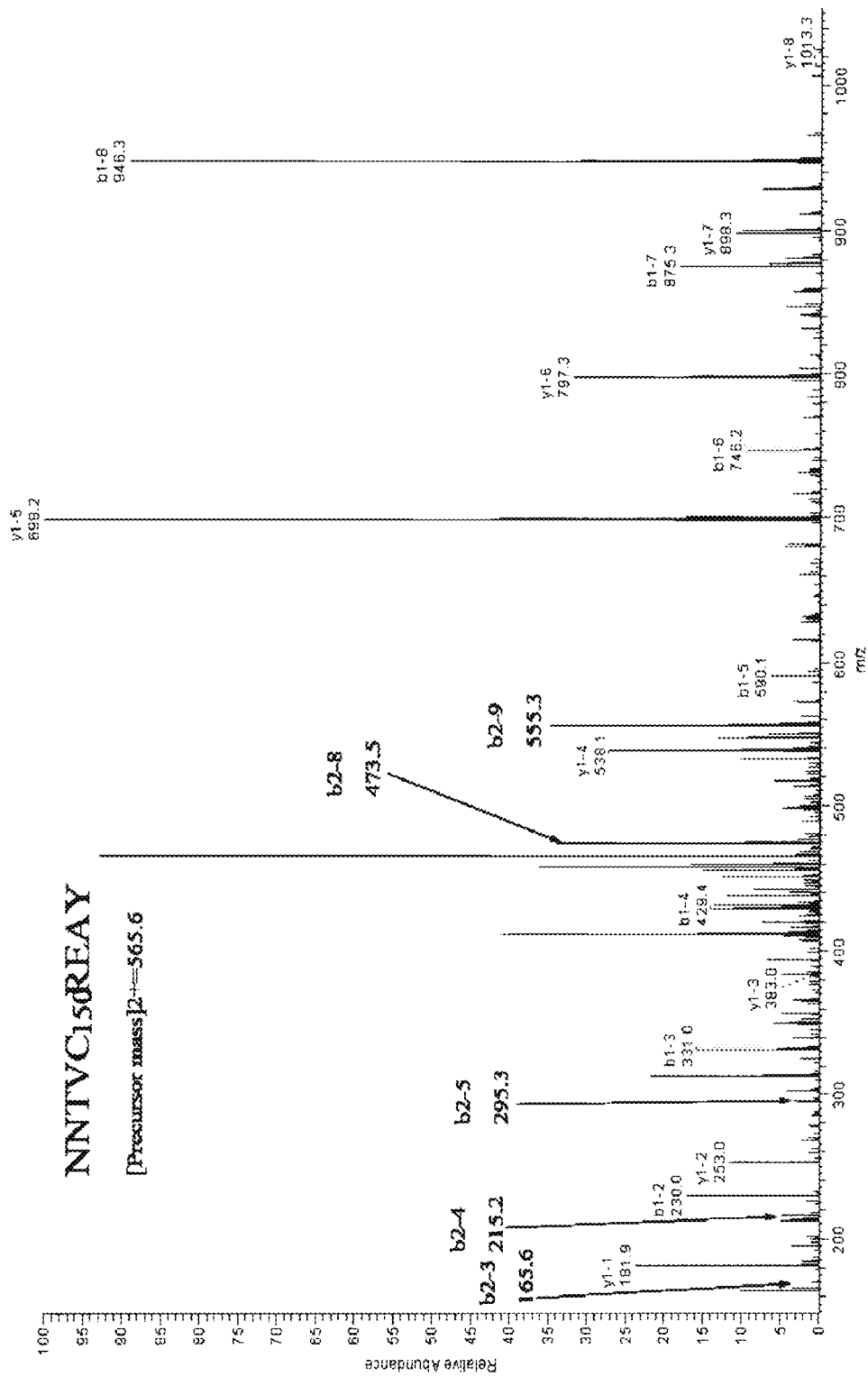
Figure 12A:
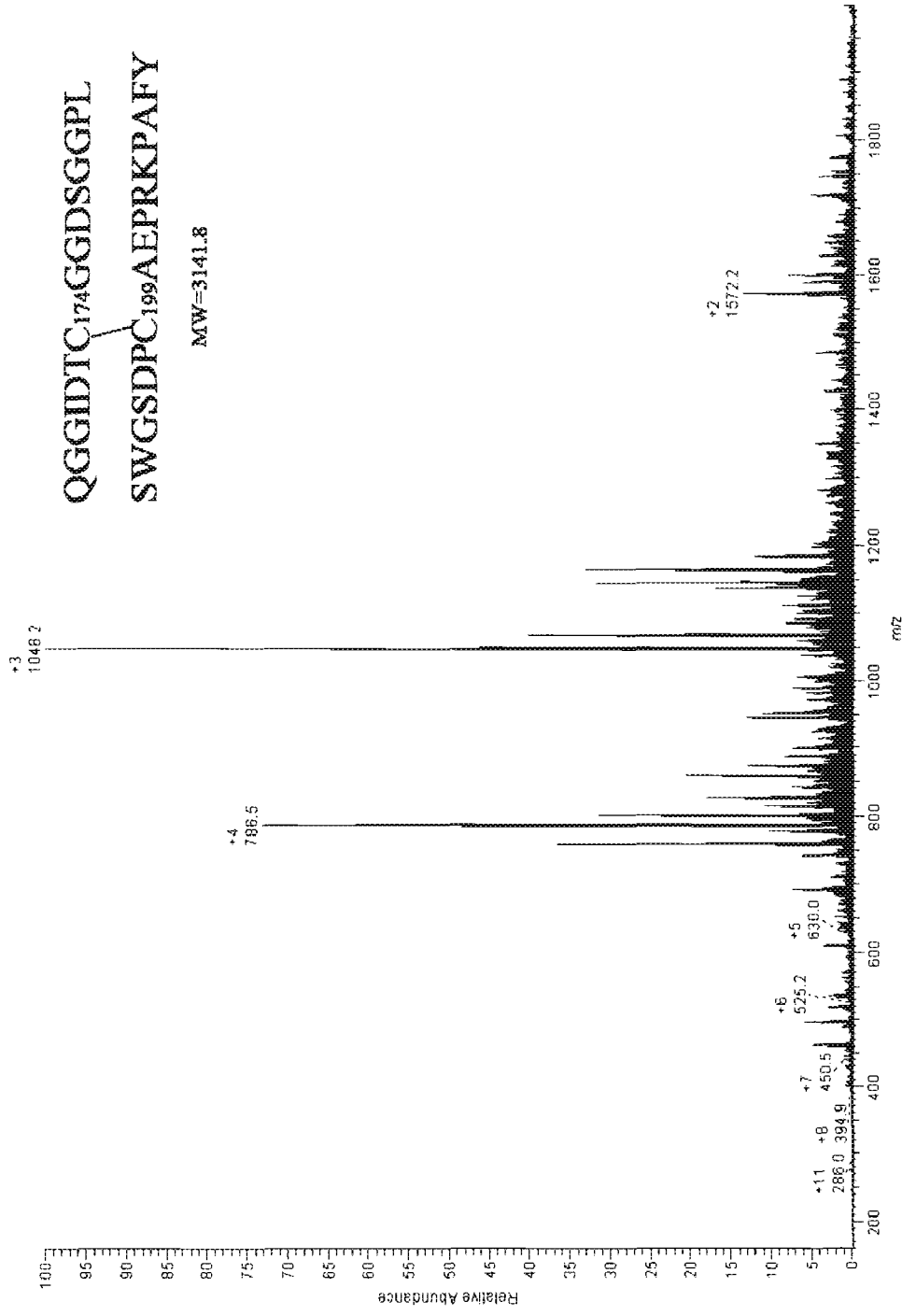
Figure 12B:
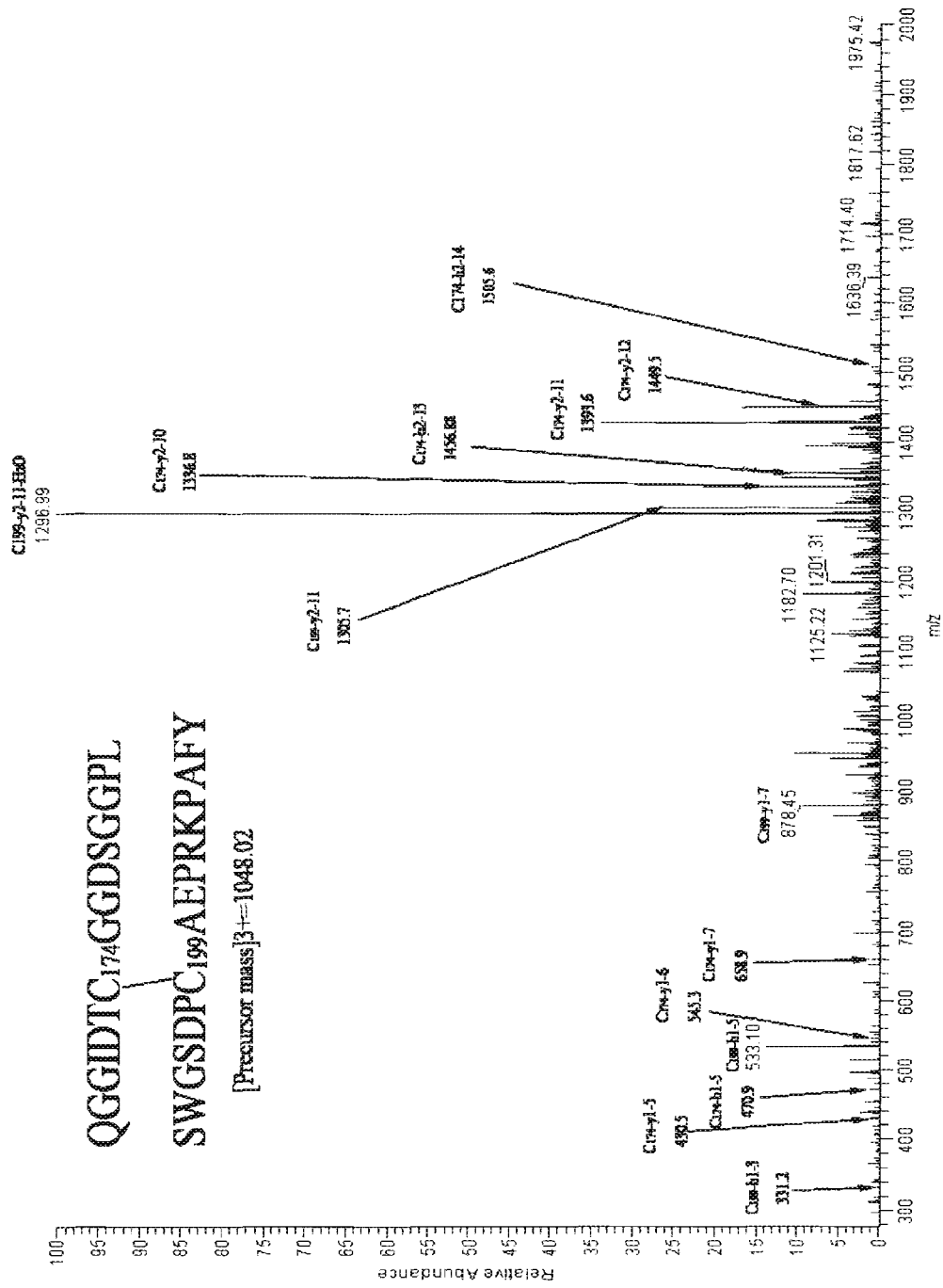
Figure 12C:
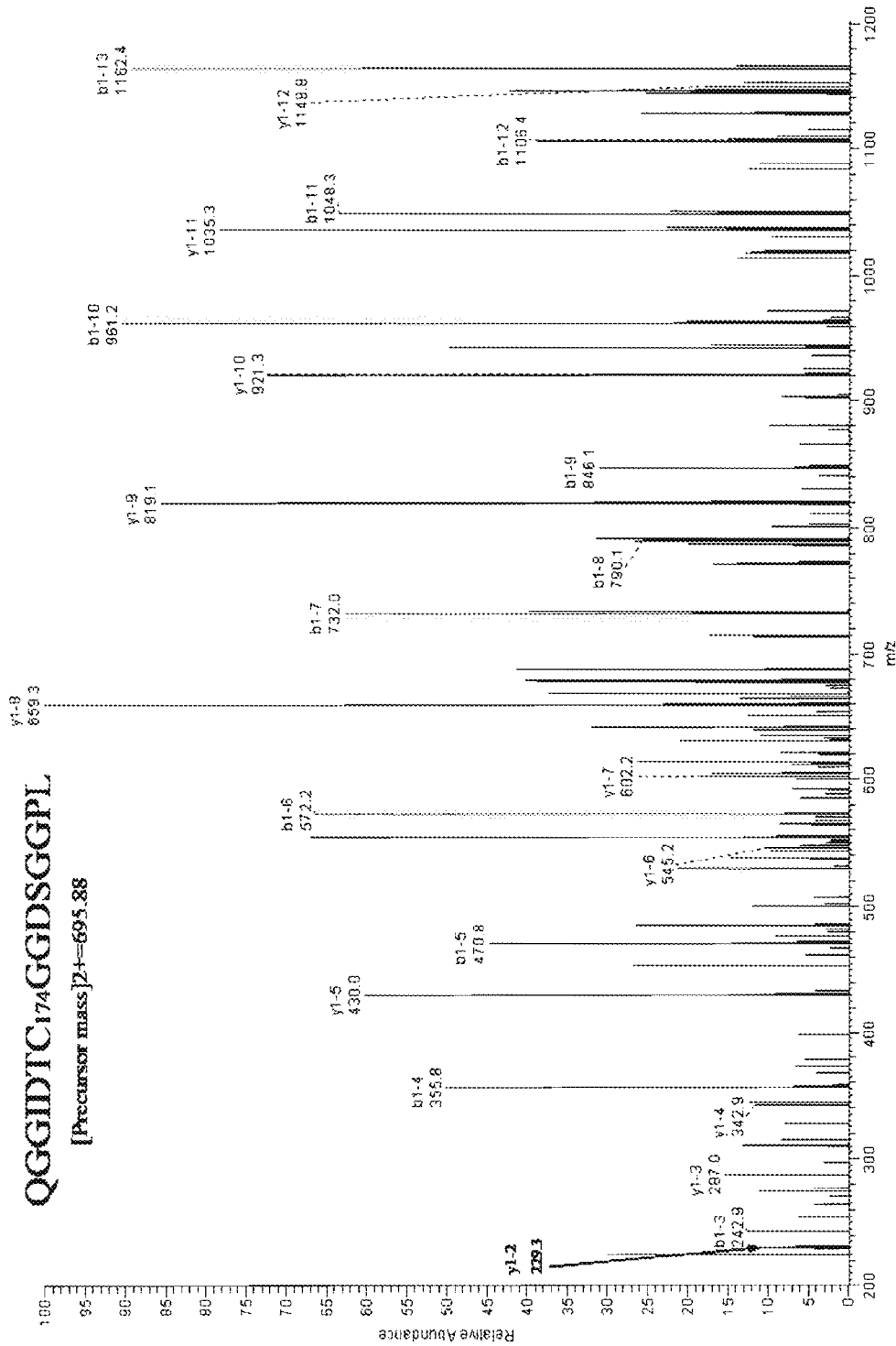
Figure 12D:
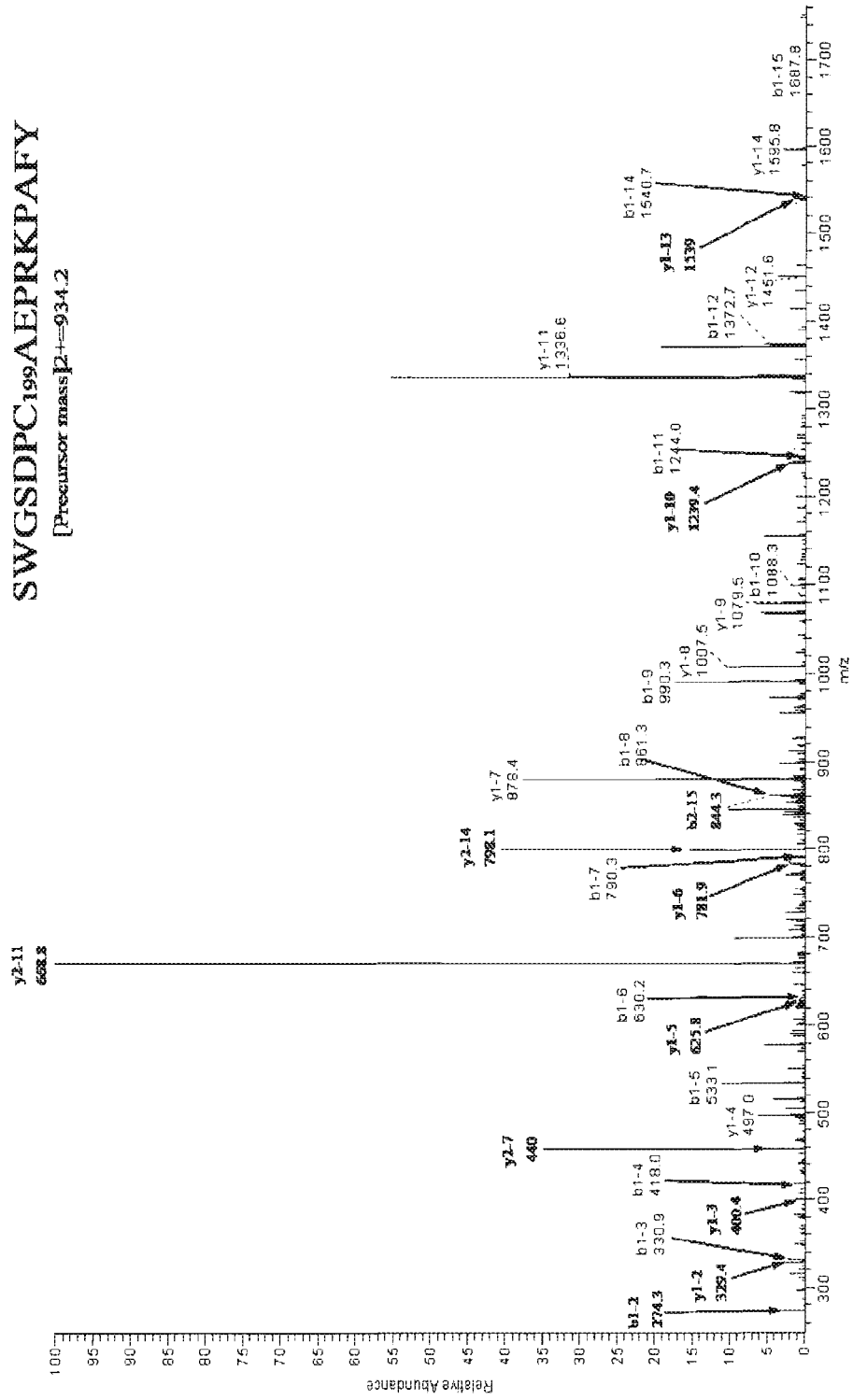

FIGS. 11A-11C shows detection pictures of disulfide bond C150-C163, wherein 11A shows the mass charge ratio m/z map of the peptide segment containing disulfide bind C150-C163;

11B shows the MS/MS map of the peptide segment containing disulfide bind C150-C163, C shows the MS/MS map of the peptide segment containing cysteine C150.

FIGS. 12A-12D shows the detection pictures of disulfide bond C174-C199, wherein 12A shows the mass charge ratio m/z map of the peptide segment containing disulfide bind C174-C199;

12B shows the MS/MS map of the peptide segment containing disulfide bind C174-C199;

12C shows the MS/MS map of the peptide segment containing cysteine C174;

12D shows the MS/MS map of the peptide segment containing cysteine C199.

FIG. 13 shows a non-reduced electrophoresis map of a fermentation broth and an ultrafiltrate supernatant, in which lane 1 represents a protein Marker, lane 2 represents a fermentation supernatant before ultrafiltration, lane 3 represents an eluate obtained by ultrafiltration, and lane 4 represents a fermentation supernatant after ultrafiltration.

FIG. 14 shows an elution map and an electrophoresis map (non-reduced SDS-PAGE) after a cation-exchange chromatography. Lane 1 represents a protein Marker, lane 2 represents a fermentation supernatant after ultrafiltration, lane 3 represents an eluate from cation-exchange, lane 4 represents an eluate of 20 mM NaAc—HAc+0.15M NaCl, lane 5 represents an eluate of 20 mM NaAc—HAc+0.50M NaCl, and lane 6 represents an eluate of 20 mM NaAc—HAc+11.0M NaCl.

FIG. 15 shows an elution map and an electrophoresis map (non-reduced SDS-PAGE) after an anion-exchange chromatography. Lane 1 represents a protein Marker, lane 2 represents an eluate of the target protein from a cation-exchange, lane 3 represents an eluate from a loading liquid for anion-exchange, lane 4 represents an eluate of 20 mM Tris-HCl+ 0.15M NaCl, and lane 5 represents an eluate of 20 mM Tris-HCl+0.50M NaCl.

FIG. 16 shows an elution map and an electrophoresis map after a gel filtration chromatography. Lane 1 represents a protein Marker, lane 2 represents a fermentation supernatant after ultrafiltration, lane 3 represents an rBAT eluate from a cation-exchange, lane 4 represents an rBAT eluate from an anion-exchange, and lanes 5-7 represent the rBAT stock solution.

FIG. 17 shows the amino acid sequence of batroxobin (SEQ ID NO:1), in which the glycosylated sites are underlined.

SPECIFIC MODE FOR CARRYING OUT THE INVENTION

After extensive and intensive investigation, the inventors have prepared a recombinant batroxobin with high specific activity by modifying the processes for expression and purification of batroxobin. The batroxobin possesses the following properties:

(a) it has a molecular weight of 30-32 kDa;

(b) at least 90% of batroxobin in said recombinant batroxobin have 6 pairs of disulfide bonds which correctly match at $Cys^7$-$Cys^{139}$, $Cys^{26}$-$Cys^{42}$, $Cys^{74}$-$Cys^{230}$, $Cys^{118}$$Cys^{184}$, $Cys^{150}$-$Cys^{163}$ and $Cys^{174}$-$Cys^{199}$;

(c) positions 146 and 225 in SEQ ID NO:1 are modified as N-glycosylation; and (d) the specific activity of the batroxobin is greater than 1500 KU/mg protein.

After successfully secreting and expressing a biologically active batroxobin of *Bothrops atrox* in *Pichia pastoris*, a multiple steps of chromatography and purification are carried out to obtain a purified batroxobin having a purity of equal to or higher than 95%.

As used herein, 1 KU is calculated as follows. 0.1 ml of human standard plasma is placed into the detection cup of a standard coagulometer (C2000-4 Type Coagulometer, Beijing Precil Instrument Co., Ltd.), and pre-heated at 37° C. for 3 minutes. Then 0.1 ml of suitable batroxobin dilution to be tested is added, and the time is measured. If the plasma is clotted at 60±20 seconds, then 1 ml of the solution to be tested contains 1 KU of batroxobin.

The gene recombinant batroxobin provided in the subject invention is a single-chain protein consisting of 231 amino acid residues (SEQ ID NO:1), with a molecular weight of 29-32 kDa and two N-glycosylated sites, $Asn^{146}$-$Asn^{147}$-$Thr^{148}$ and $Asn^{225}$-$Lys^{226}$-$Thr^{228}$.

In the gene recombinant batroxobin provided in the subject invention, at least 90%, preferably at least 95%, more preferably at least 98%, of the batroxobin possess 6 pairs of disulfide bonds which correctly match in the following manners: $Cys^7$-$Cys^{139}$, $Cys^{26}$-$Cys^{42}$, $Cys^{74}$$Cys^{230}$, $Cys^{118}$-$Cys^{184}$, $Cys^{150}$-$Cys^{163}$ and $Cys^{174}$-$Cys^{199}$.

The gene recombinant batroxobin provided in the subject invention exhibits a specific activity of equal to or greater than 1500 KU/mg protein, preferably 1500-2000 KU/mg, more preferably 1500-3000 KU/mg.

The gene recombinant batroxobin provided in the subject invention is produced by using the codons for which *Pichia pastoris* has a preference to manually synthesize the gene sequence of batroxobin, constructing an expression vector and finally obtaining a biologically active batroxobin of *Bothrops atrox* in *Pichia pastoris*. It was found by the inventors that the eucaryotic cell expression system (yeast, CHO and insect cells and the like) can ensure a relatively high rate of correct matching of disulfide bond and the post-modification of the expressed protein. The inventors have successfully expressed the batroxobin protein having a biologically activity in Methylophic yeast (*Pichia pastoris, Pichia methanolica*), with an output of 20 KU/ml fermentation broth. The output is significant in developing the recombinant batroxobin protein.

By isolating and purifying the fermentation supernatant, a purified recombinant batroxobin is obtained. In one preferred embodiment of the invention, said purification step comprises ultrafiltration, cation-exchange chromatography, anion-exchange chromatography and gel chromatography. By optimizing the chromatography conditions, a highly purified recombinant batroxobin with a high rate of correct matching of disulfide bond and a strong specific activity is obtained.

The fermentation supernatant obtained in the subject invention contains a great amount of protein impurities, inorganic salts, pigments and the like. Therefore, the invention firstly uses the ultrafiltration to desalt, remove the protein impurities and replace the buffer, so as to facilitate the subsequent ion-exchange chromatography. The conditions for carrying out the ultrafiltration include an input pressure of 5-10 psi, an output pressure of 2-5 psi and a flow rate of 100-200 ml/min. The pH value of the balancing buffer for ultrafiltration is 4-6, preferably 4.5-5.5. The balancing buffer system for ultrafiltration may be the salts conventionally used in the art, includes but is not limited to sodium acetate, sodium phosphate, sodium citrate and Tris-HCl, wherein sodium acetate-acetate and sodium chloride are preferred. The electric conductivity of the obtained ultrafiltration solution is below 8 mS/cm, preferably below 5 mS/cm, and more preferably below 4 mS/cm.

Then, the fermentation supernatant after ultrafiltration is subjected to a cation-exchange chromatography. The cation-exchange chromatography column conventionally used in the art can be used and includes but is not limited to SP Sepherose FF and CM Sepherose FF, wherein SP Sepherose FF is preferred. The elution buffer has a pH value of 4-6, preferably 4.5-5.5. The buffer may be the salts conventionally used in the art which include but are not limited to sodium acetate, sodium phosphate and sodium chloride, with sodium acetate-acetate and sodium chloride preferred. In the buffer, the concentration of sodium chloride may be 0.1-1.0M, preferably 0.15-1.0M, and more preferably 0.4-0.6M. One preferred manner for elution is the gradient elution.

In the third step, the eluate obtained after passing through the cation-exchange chromatography column is subjected to an anion-exchange chromatography. The anion-exchange chromatography column conventionally used in the art could be used, which includes but is not limited to Q Sepherose, DEAE Sepherose, and Source 30Q, with Q Sepherose FF preferred. The elution buffer has a pH value of 7.5-10, preferably 8.5-9.5. The buffer may be the salts conventionally used in the art, include but are not limited to Tris-HCl, sodium phosphate and sodium chloride, with Tris-HCl and sodium chloride preferred. In the buffer, the concentration of sodium chloride may be 0.05-1.0M, preferably 0.10-0.6M, more preferably 0.15-0.5M. One preferred manner for elution is the gradient elution.

Finally, the eluate obtained after passing through the anion-exchange chromatography column is subjected to a gel filtration chromatography. The gel filtration chromatography column conventionally used in the art can be used and includes but is not limited to Sephacryl S, Sepharose 4, Sephadex G-25 and Superdex, wherein Superdex 75 is preferred. The elution buffer has a pH value of 4-6, preferably 4.5-5.5. The buffer may be the salts conventionally used in the art, and includes but are not limited to sodium acetate, sodium phosphate and sodium chloride, wherein sodium acetate-acetate and sodium chloride are preferred. In the buffer, the concentration of sodium chloride may be 0.05-0.5M, preferably 0.10-0.3M, and more preferably 0.12-0.2M.

The purified gene recombination batroxobin of the subject application can be obtained after the above steps. Alternatively, one may use the well-known genetic engineering method known in the art to obtain a fermentation solution containing batroxobin protein, and then purify according to the above steps to obtain the gene recombinant batroxobin of the present invention.

The gene recombinant batroxobin of the subject invention can be used in hemostasis. The specific substrate of batroxobin is fibrinogen. Unlike thrombin, batroxobin only cleaves the A chain of fibrinogen rather than the B chain. When hydrolyzing the peptide bond between Arg16 and Gly17 in the A chain of fibrinogen, batroxobin can release fibrinopeptide A, thus quickly converting the fibrinogens in blood into fibrins. And then the fibrins can aggregate to form loose thrombus, which can be hydrolyzed by brinase, to block the wound so as to produce the efficacy of quick hemostasis. However, when using a relatively high dosage, batroxobin can reduce the concentration of fibrins in blood, improve the blood viscosity and the fluid mechanics properties of blood, and thus produce the efficacy of defibrase (U.S. Pat. No. 3,849,252, 1974).

The invention further provides a pharmaceutical composition, which comprises the purified gene recombinant batroxobin of the subject invention and a pharmaceutically acceptable carrier.

The pharmaceutical composition of the invention may further contain a hydrolyzed gelatin as a stabilizer. The pharmaceutical composition of the subject invention can be a liquid or a freeze-dried powder, wherein the liquid form is preferred and the injection solution is more preferred.

The main advantages of the subject invention include:

1. The gene recombinant batroxobin of the subject invention exhibits a greatly high rate of correct matching of disulfide bond.

2. The gene recombinant batroxobin of the subject invention has a high specific activity.

3. The subject invention provides an isolation and purification method for obtaining the above gene recombinant batroxobin with excellent quality.

The invention is further illustrated by the following examples. It should be appreciated that these examples are only intended to illustrate the invention, but not to limit the scope of the invention. For the experimental methods in the following examples, they are performed under routine conditions, such as those described in Sambrook et al., Molecular Cloning: A Laboratory Manual, New York: Cold Spring Harbor Laboratory Press, 1989, or as instructed by the manufacturers, unless otherwise specified. Unless otherwise specifically indicated, all of the percentages and parts are calculated by weight.

EXAMPLE 1

Preparation Example

1. Preparation of Fermentation Broths Containing Batroxobin Protein

Fermentation of rBAT gene-engineering yeast in 30 L fermenter:

The rBAT gene-engineering yeast was inoculated in a inoculation rate of 1:10 into a 30 L fermenter, which was sterilized beforehand and filled with 15 L of batch fermentation media, and then the media for culture was supplemented in batch. The pH was controlled with ammonium hydroxide at 4.0, and the temperature was controlled at 30° C. After carbon source was exhausted (within 1 minute when DO suddenly increased), glycerol was added in such a rate that the dissolved oxygen (DO) was maintained under 20%. After the wet weight of yeast cell was about 200 grams per liter, the supplementing media was stopped. After glycerol was depleted, methanol was added to induce expression, wherein the pH was controlled with ammonium hydroxide at 4.0, and the temperature was controlled at 20° C. By regulating the agitation, the pressure of the fermenter, the aeration and the rate of supplementing media, the dissolved oxygen was maintained to no less than 20%. The induction time was 60 hours. After fermentation, the fermentation supernatant was collected by centrifugation at 4000 rpm. By detecting the activity, it was confirmed that the expression output should not be lower than 20 KU/ml. The fermentation supernatant was stored by freezing or directly purified.

2. Isolation and Purification

Step 1: Replacement of buffer by ultrafiltration. Millipore Pellicon 10K ultrafiltration membrane stack, and Millipore Masterflex peristatic pump were used. The input pressure and output pressure of the ultrafiltration instrument were controlled to be 6 psi and 3 psi, respectively. The flow rate was 120 ml/min. After equilibrium of the ultrafiltration membrane successively with water for injection and buffer of 20 mM NaAc—HAc+0.15M NaCl (pH 5.0), the fermentation supernatant was subjected to ultrafiltration. During ultrafiltration, when the volume of the solution reached ⅕ of the original volume, buffer of 20 mM NaAc—HAc (pH 5.0) was added to the original supernatant volume, and such operation was repeated for three times. Then, a buffer of 20 mM NaAc—HAc (pH 5.0) was added to the original volume, and the resulted solution was used as a loading sample for cation-exchange chromatography.

Step 2: Cation-exchange chromatography. The SP Sepharose F F was filled. The equilibrium buffer was 20 mM NaAc—HAc (pH 5.0), the elution buffers were 20 mM NaAc—HAc+0.15M NaCl (pH 5.0), 20 mM NaAc—HAc+0.50M NaCl (pH 5.0), and 20 mM NaAc—HAc+1.0M NaCl (pH 5.0), respectively. The eluate of 20 mM NaAc—HAc+0.50M NaCl (pH 5.0) was collected.

Step 3: Anion-exchange chromatography (Q Sepharose FF). The pH of the eluate of 20 mM NaAc—HAc+0.50M NaCl (pH 5.0) obtained from the cation-exchange chromatography was adjusted to 9.0, and the sample was diluted so that its electric conductivity was 3.0 mS/cm, and then the sample was loaded. The equilibrium buffer was 20 mM Tris-HCl (pH 9.0), the elution buffers were 20 mM Tris-HCl+0.15M NaCl (pH 9.0), 20 mM Tris-HCl+0.50M NaCl (pH 9.0), respectively. The eluate of 20 mM Tris-HCl+0.15M NaCl (pH 9.0) was collected.

Step 4: Gel filtration chromatography. The Superdex 75 was filled with 6.0×60 cm prepacked column, CV1700 ml. The buffer was 20 mM NaAc—HAc+0.15M NaCl (pH 5.0). The eluate of 20 mM Tris-HCl+0.15M NaCl (pH 9.0) from the anion-exchange chromatography was loaded in batch and the rBAT main peak was collected in stages. The samples with a purity of higher than 95% were pooled and sterilized to obtain the rBAT stock solution 1.

EXAMPLE 2

Property Example

The rBAT stock solution I obtained in Example 1 was detected as follows:

1. Main Experimental Parameters:
Model of the detection apparatus: LCQ DECA XP plus
Manner of loading: Microspray
Temperature of capillary tube: 170° C.

Chromatographic column: 0.15 MM*150 MM (RP-C18)
Company of the apparatus: FINNIGAN
Detection Manner: positive ion 2. Experimental Method:

The sample rBAT was subjected to ultrafiltration for desalting, modification by iodoacetamide (IAA), enzymolysis by trypsin and chymotrypsin, enzymolysis by N-glycosidases F and F1, reduction of ½ of the enzymolysis products by dithiothreitol(DTT), IAA modification, mass spectrum analysis and data analysis so as to confirm the C end sequence of rBAT protein, the glycosylated sites, and the match manner of the disulfide bond.

3. Experimental Results and Analysis:

3.1 Analysis on the C End Sequences

Principle of identifying the C-Terminal of rBAT protein by mass spectrum: The protein to be tested was digested by protease to obtain the peptide segment containing the C-terminal sequences. Then, the similarity (Xcorr) of the secondary mass spectrum obtained by the experiments and the theoretical one was compared, thereby verifying the C-terminal sequence.

Figure 1:
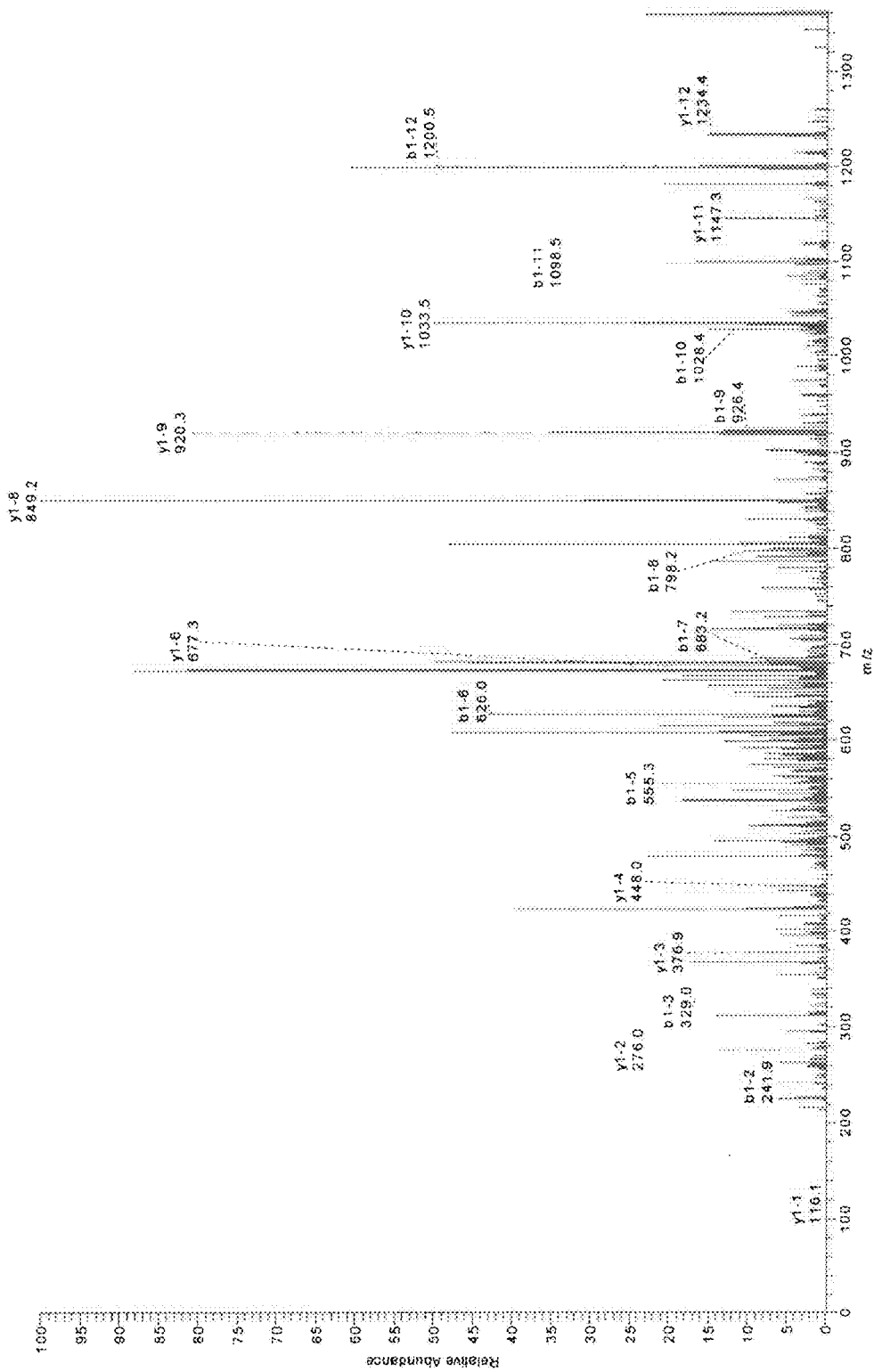
FIG. 1 shows the C-terminal sequence of the gene recombinant batroxobin of the invention and it shows that there is a glycosylation modification at Asn225.

If the rBAT protein was not treated by the N-glycosidase F (PNGase F) for de-glycosylation, then it was unable to confirm the C-terminal sequence of the rBAT protein. However, when subjecting the enzymolysis products of rBAT to N-glycosidase F (PNGase F) for deglycosylation, the experimental data were well consistent with the theoretical second mass spectrum, and the C-terminal sequence could be verified as IQSIIAGDKTATCP (SEQ ID NO: 2). It should be noted that when the saccharide chain linked to Asn was removed by PNGase F, it also converted the Asn into Asp. And, at the same time, Cys was also modified to be acetylated cysteine. The experimental results were shown in FIG. 1. In the experiments, a series of b and y ions were observed, such as b2, b3, b5-b12, y1-y4, y6, and y8-y12. The b and y ions were the fragment ions commonly found in the experiment, which were produced due to the disruption of the peptide chain of the peptide segment. If the charge after disruption was at the N-terminal of the peptide segment, then the ion was a b ion. If the charge was at the C terminal of the peptide segment, then the ion was a y ion. As indicated in FIG. 1, the y1-8 ions represented GDKTATCP+ (SEQ ID NO: 3), the y ion represented that said ions were the ions of the y series, 1 represented that the charge number of said ion was 1, and 8 indicated the position where the peptide bond was disrupted.

3.2 Determination of the Glycosylated Sites

Principle of determining the glycosylated sites: The protein to be tested was digested with protease to obtain peptide segments with different sizes. Then, a part of the sample obtained after digestion by enzyme was treated by PNGase F to cleave the saccharide chain linked at Asn and convert Asn into Asp. And then the sample subjected to the deglycosylation and the sample not subjected to the deglycosylation were subjected to HPLC-MS-MS analysis, respectively. By comparing the percentage of coverage of the peptide segment obtained by the experiments, it could determine whether or not there was glycosylated modification and sites with glycosylated modification.

Figure 2:
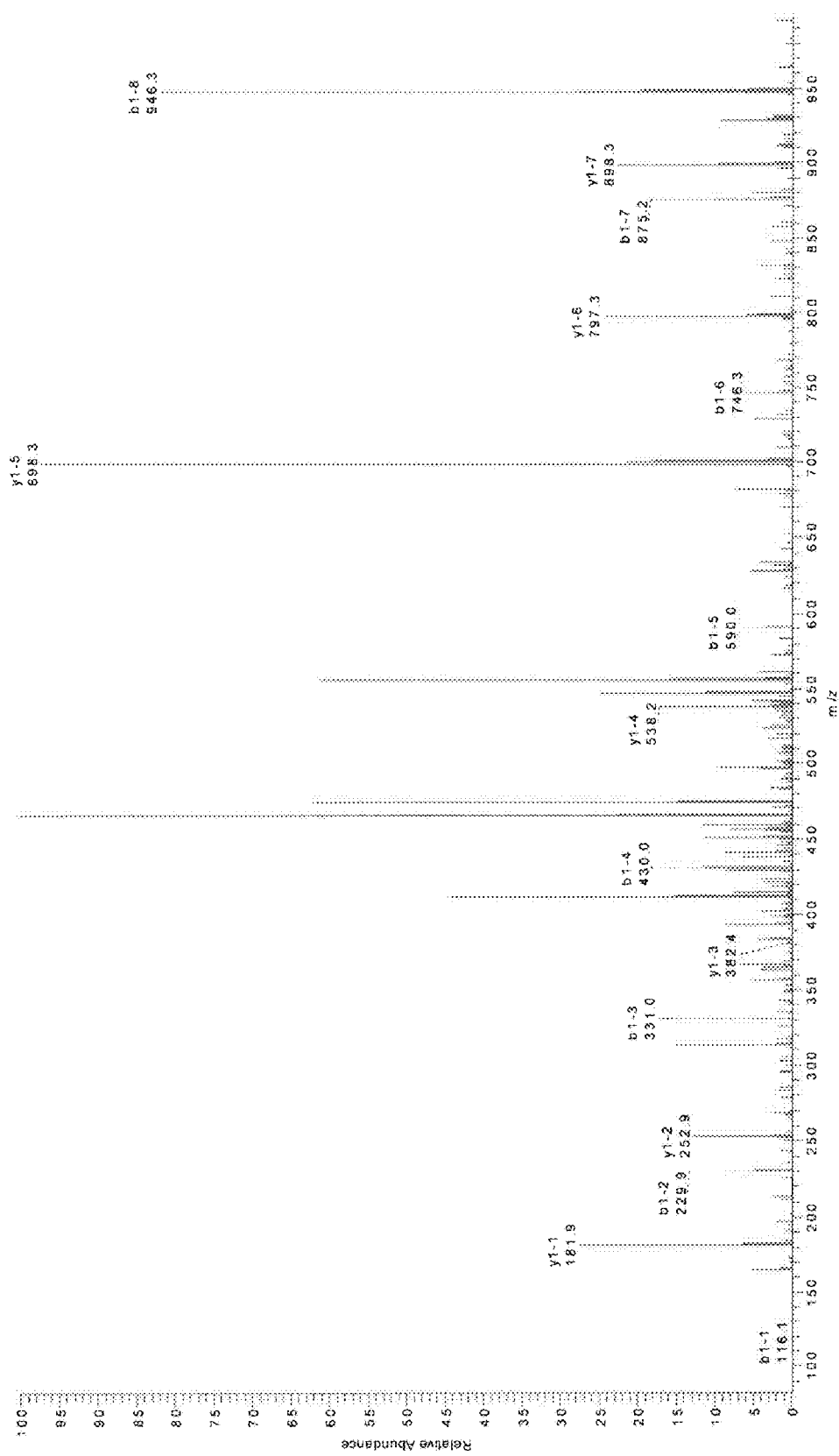
FIG. 2 shows that there is a glycosylation modification at Asn146 in the gene recombinant batroxobin of the invention.
Figure 3:
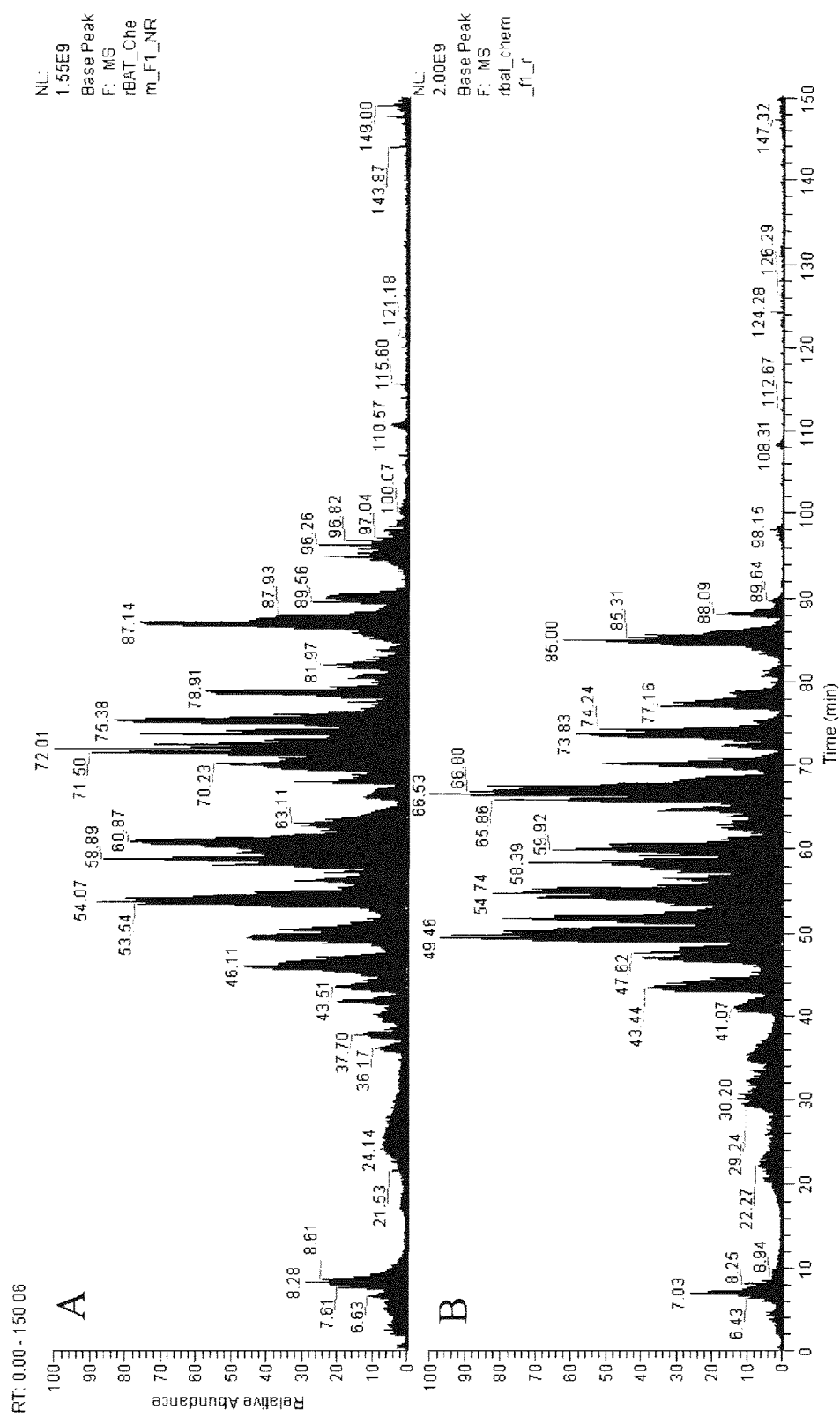
FIG. 3 shows (A) the Base Peak of enzymolysis of rBAT with Chymotrypsin and F1 enzyme in the non-reduced condition and (B) the Base Peak of enzymolysis of rBAT with Chymotrypsin and F1 enzyme in reduced condition.
Figure 4:
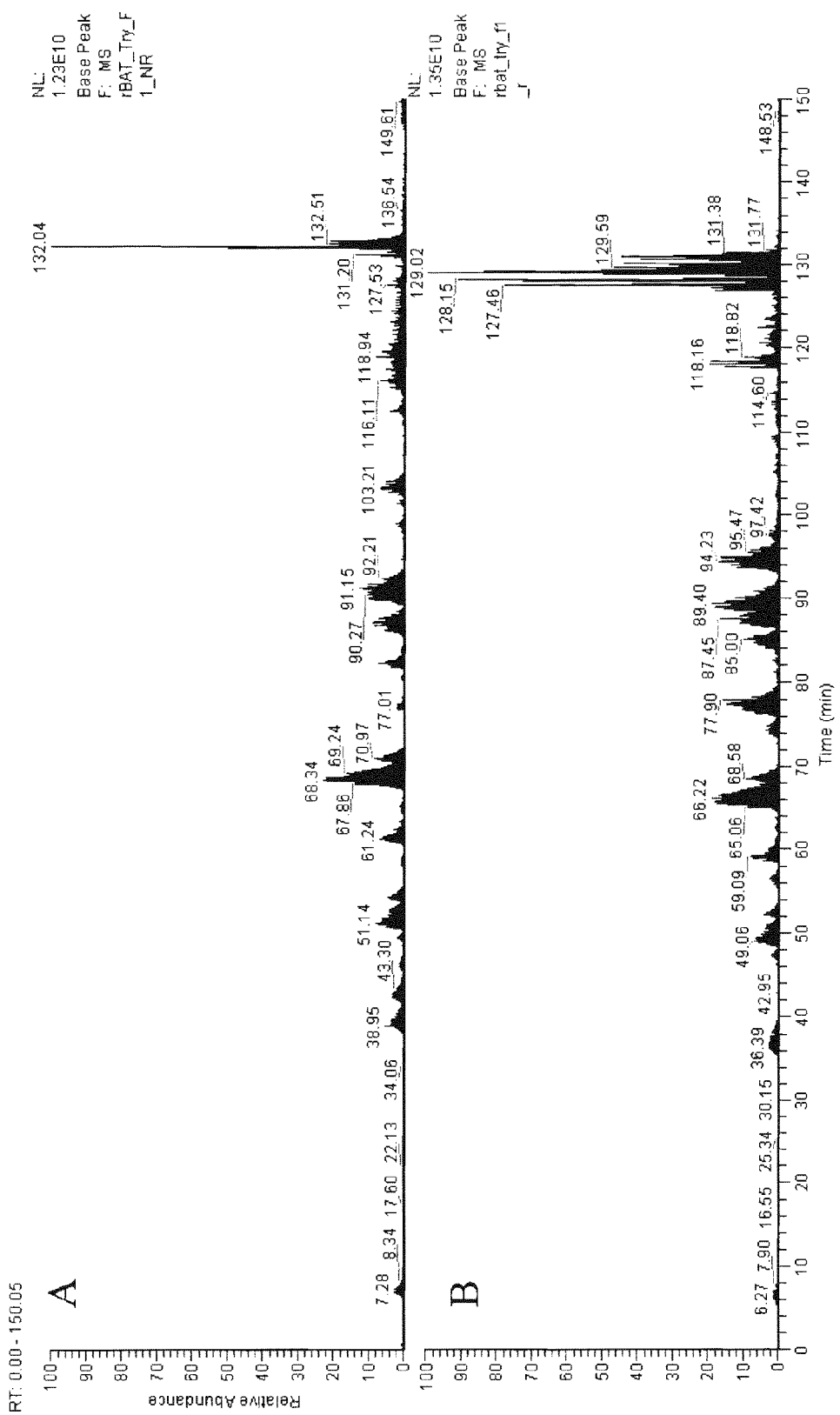
FIG. 4 shows (A) the Base Peak of enzymolysis of rBAT with Trypsin and F1 enzyme in the non-reduced condition and (B) the Base Peak of enzymolysis of rBAT with Trypsin and F1 enzyme in the reduced condition.
Figure 5:
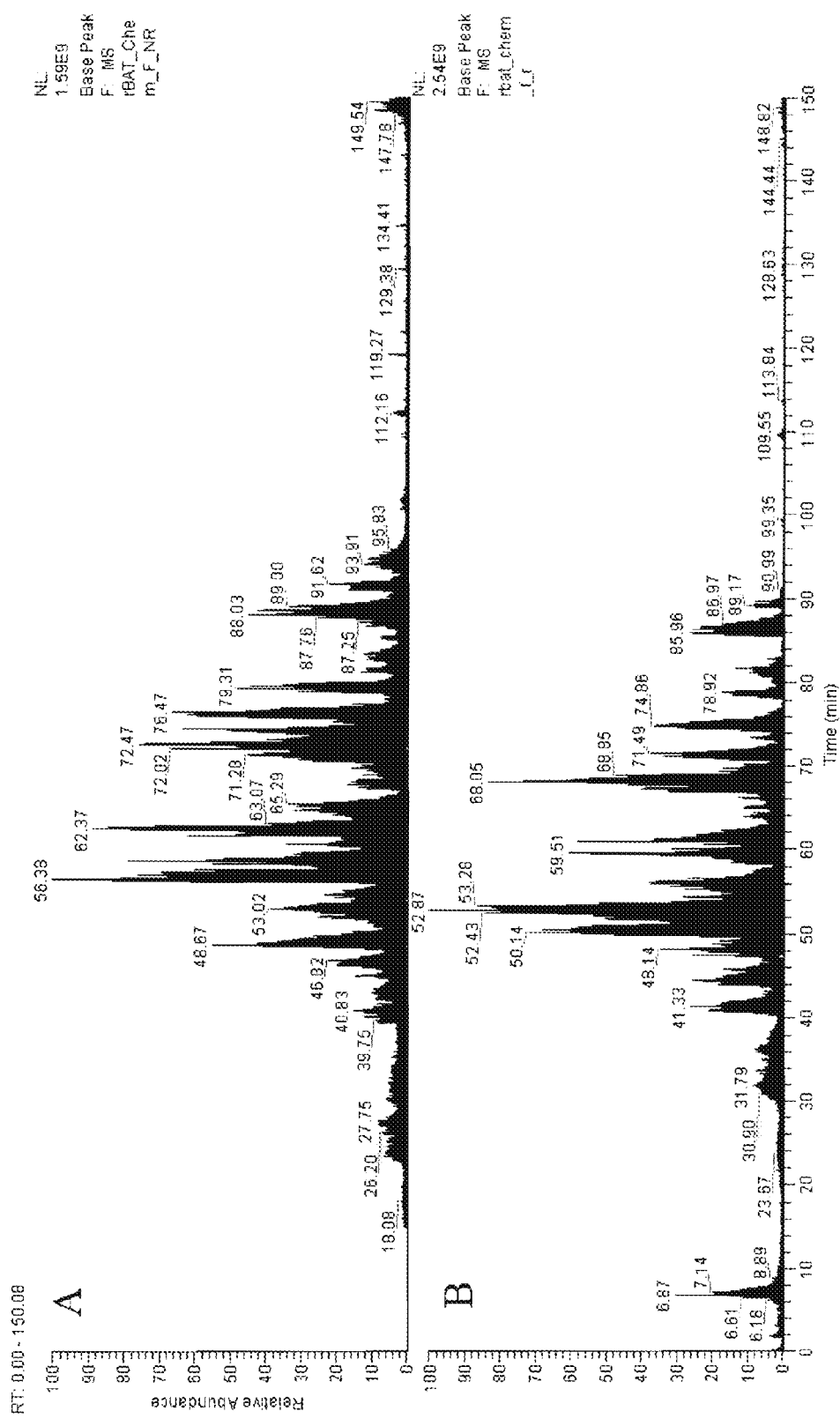
FIG. 5 shows (A) the Base Peak of enzymolysis of rBAT with Chymotrypsin and N-glycosidase F in the non-reduced condition and (B) Base Peak of enzymolysis of rBAT with Chymotrypsin and N-glycosidase F in the reduced condition.
Figure 6:
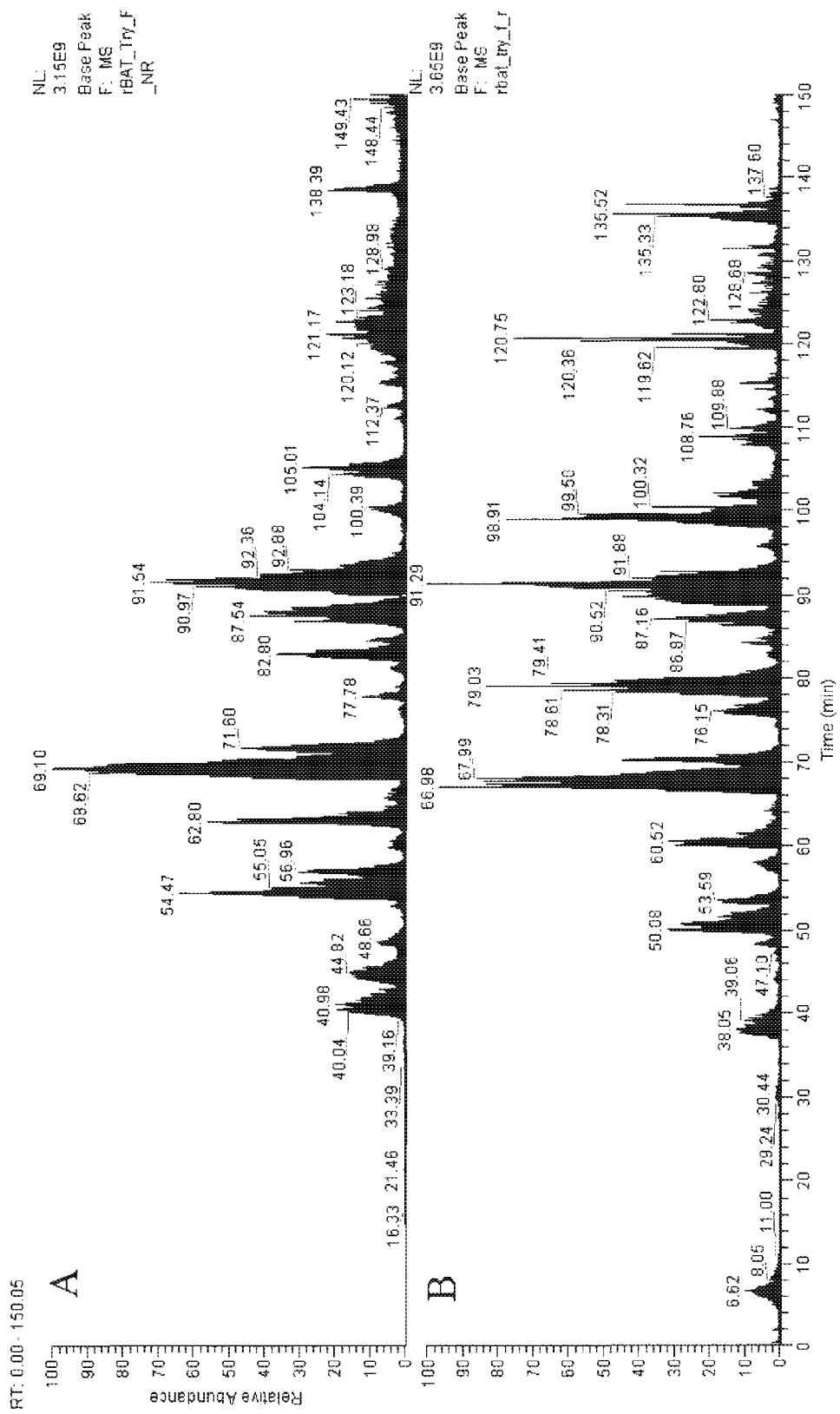
FIG. 6 shows (A) the Base Peak of enzymolysis of rBAT with Trypsin and N-glycosidase F in the non-reduced condition and (B) the Base Peak of enzymolysis of rBAT with Trypsin and N-glycosidase F in the reduced condition.

With experiments, it was found that there were two N-glycosylated sites, one was $Asn^{146}$, and the other, $Asn^{225}$. For the identification of the $Asn^{225}$ glycosylated site, see FIG. 1. For the identification of the $A^{146}$ glycosylated site, see FIG. 2.

Note: After cleaving the N-saccharide chain by N-glycosidase, Asn was converted into Asp at the same time, and Cys was also modified to be acetylated cysteine. Almost all of b and y ions were detected, such as b1-b8 and y1-8. These results sufficiently verified the sequence of said peptide segment.

3.3 The Match Manner of the Disulfide Bond

Principle of identifying disulfide bond by mass spectrometry: The free cysteines of the protein to be tested were firstly blocked by iodoacetamide (IAA). Then the protein to be tested was digested by protease under a non-reduced condition. A part of the digested product was directly subjected to a HPLC-MS-MS analysis, and the other part was reduced by dithiothreitol (DTT). The cysteines were modified by IAA to prevent formation of new disulfide bond. Finally, by comparing the difference among the peptide segments detected, new peptide segments obtained by reduction by DTT were obtained, thereby deducing the connection mode of disulfide bond. After that, by comparing the molecular weights and secondary mass spectrum maps, the connection mode of disulfide bond could be determined from the second mass spectrum map of the digested products under the non-reduced condition.

Because there were glycosylated modifications in the rBAT protein, it could be found from the above data that in the glycosylated modification sites there were cysteines. This may affect the detection of the match manner of disulfide bond. Therefore, after digestion with protease, the inventors added a step of removing the saccharide chain by PNGase F, so as to facilitate the detection for the match manner of disulfide bond. We designed four groups of control experiments as follows: rBAT-chymotrypsin-N-glycosidase F-non-reduction and rBAT-chymotrypsin-N-glycosidase F-reduction, rBAT-trypsin-N-glycosidase F-non-reduction and rBAT-trypsin-N-glycosidase F-reduction, rBAT-chymotrypsin-F1-non-reduction and rBAT-chymotrypsin-F1-reduction, and rBAT-trypsin-F1-non-reduction and rBAT-trypsin-F1-reduction. From the data obtained from the four groups, we analyzed 75 possible peptide segments containing disulfide bonds, totally 47 match manners of disulfide bonds. By using stringent screening standard, 6 pairs of disulfide bonds were detected: C7-C139, C26-C42, C74-C230, C118-C184, C150-C163 and C174-C199. Further, a minute quantity of peptide segments containing cysteine C7, C118 and C150 which did not form disulfide bond were also detected. For specific results, see FIGS. 3-6 and 8-12.

The peptide segments linking by disulfide bond were disrupted in various manners because they contained two peptide segments. It is possible that one chain was disrupted and the other peptide chain linking by disulfide bond was maintained. It was also possible that two peptide chains were disrupted respectively. The invention now illustrates a method for determining the connection mode of disulfide bond by illustrating a peptide segment linking via Cys7 and Cys139. In the experiments of rBAT-chymotrypsin-N-glycosidase F-non-reduction and rBAT-chymotrypsin-N-glycosidase F-reduction, we detected two peptide segments of VIGGDECDINEHPF (SEQ ID NO: 4) and GAITTSED-TYPDVPHCANIN (SEQ ID NO: 5) (see FIGS. 7C and 7D).

Figure 7A:
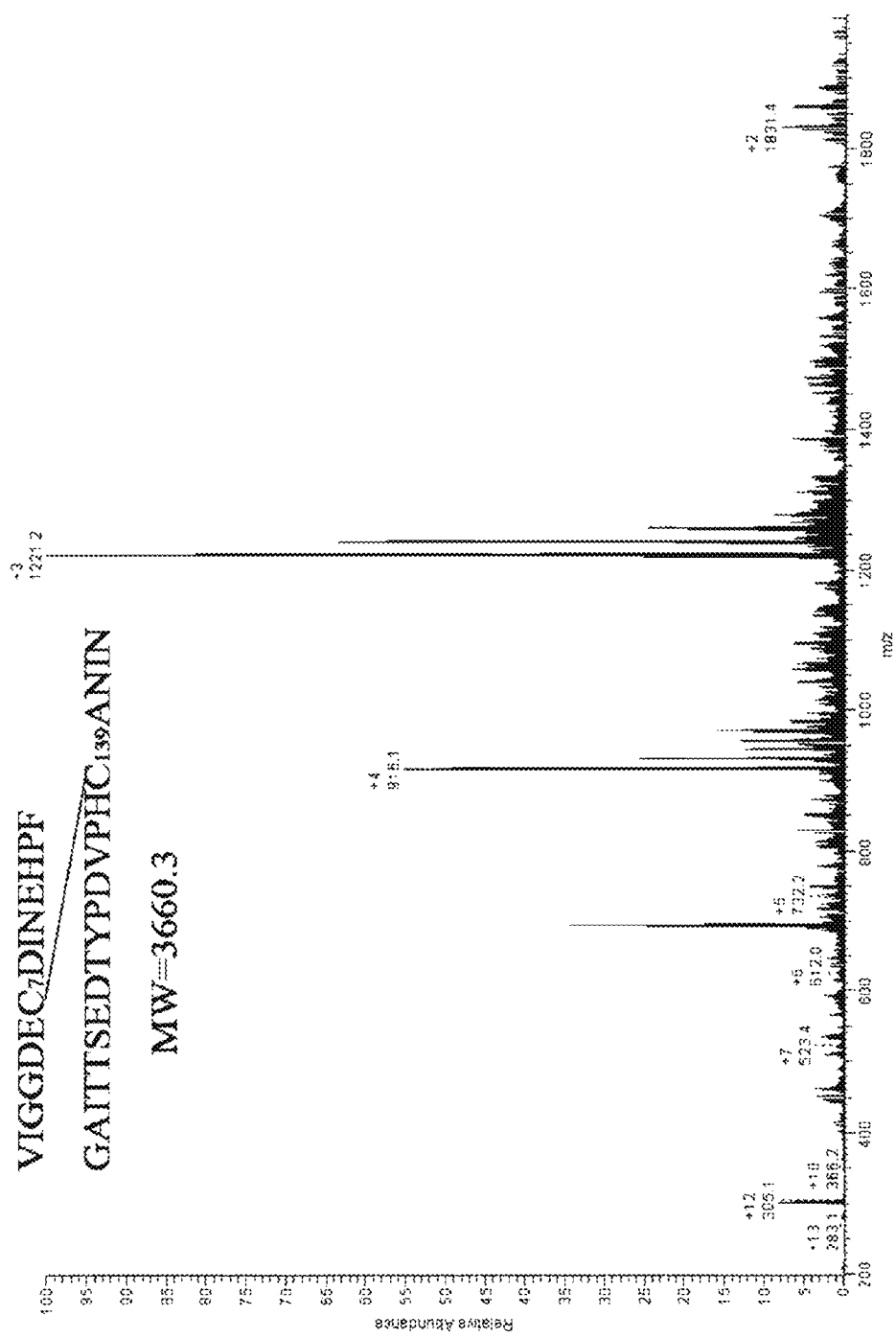
Figure 7C:
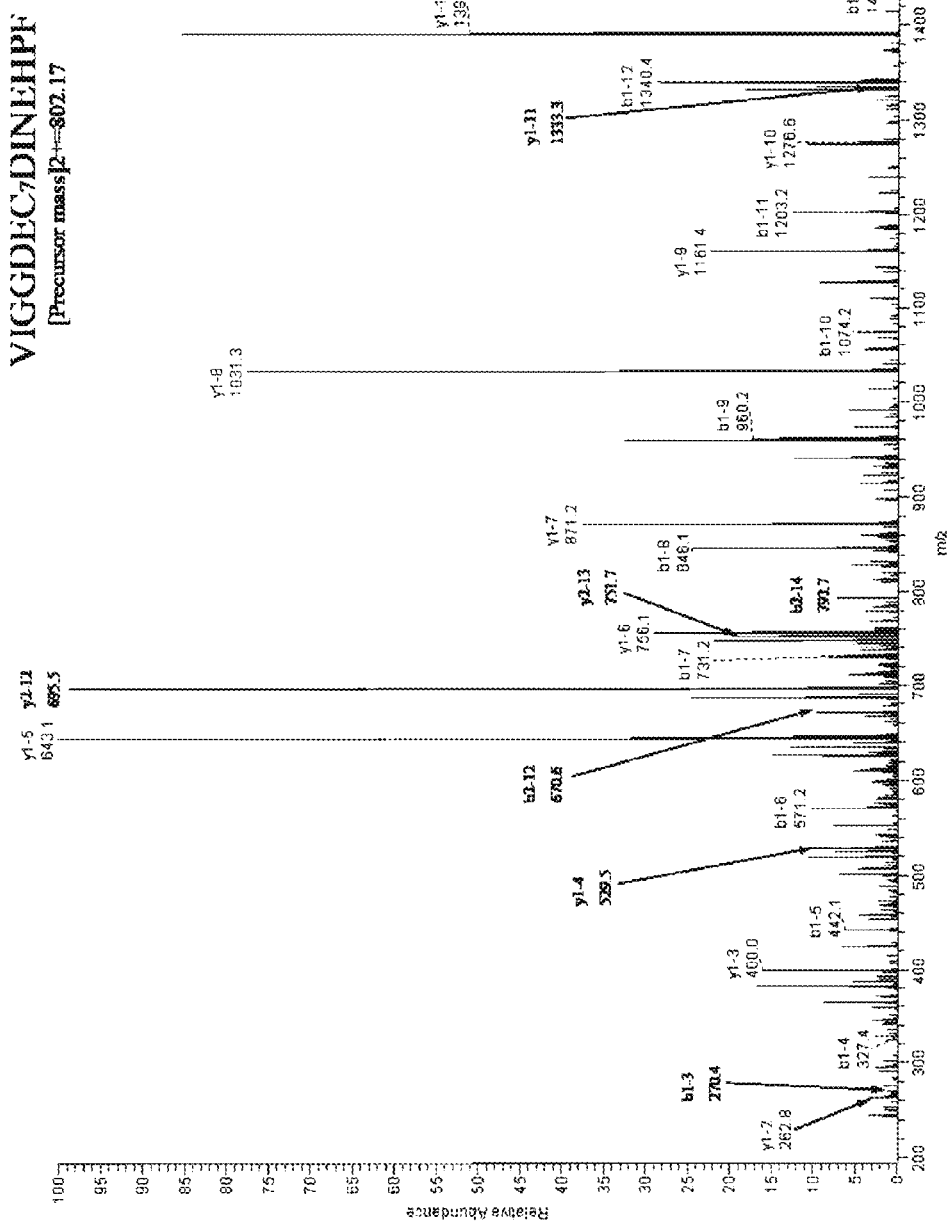
Figure 7D:
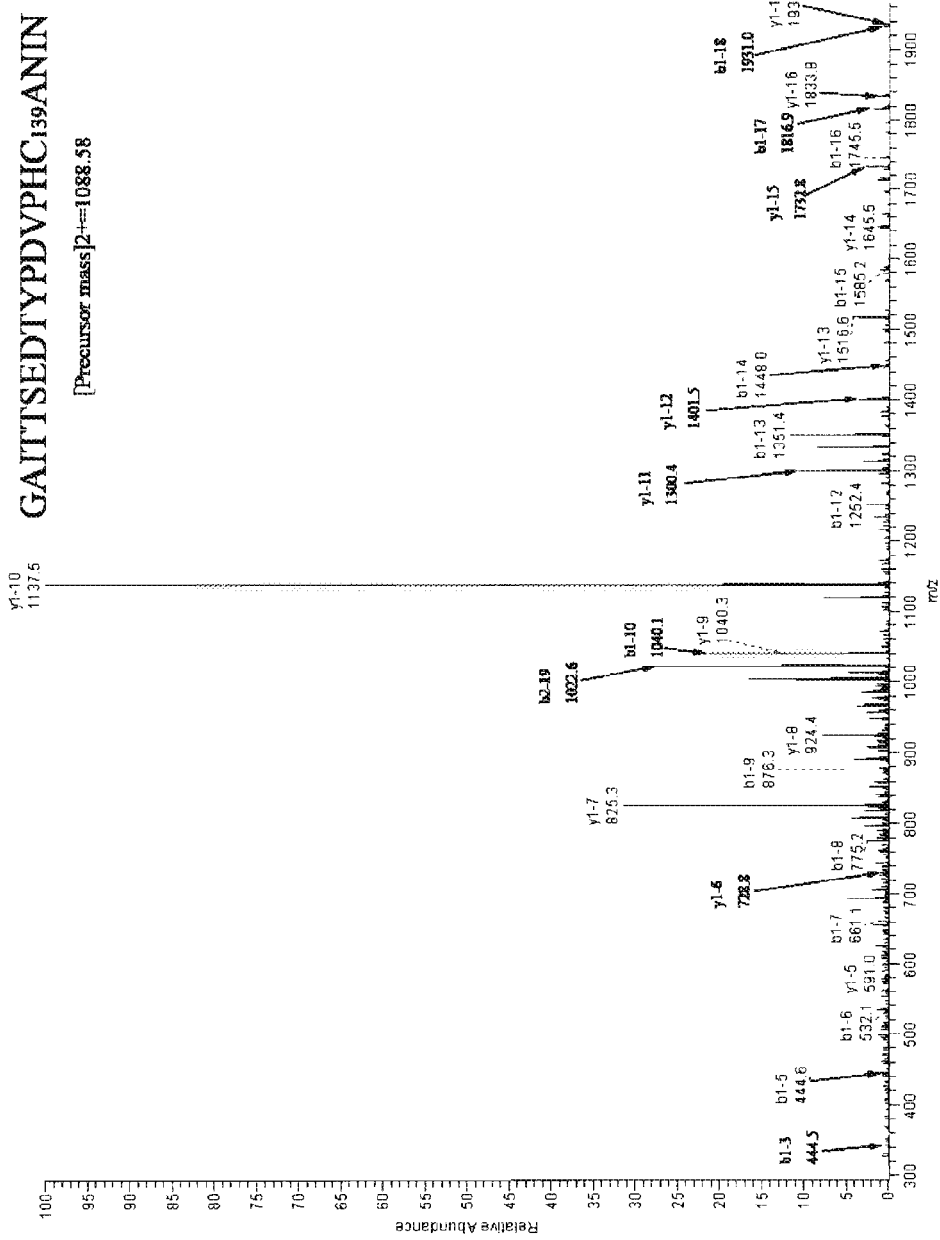

These two peptide segments were not detected in the experiment of rBAT-chymotrypsin-N-glycosidase F-non-reduction. In the non-reduced sample, peaks with charge mass ratios of 916.1 Da, 1221.3 Da and 1831.4 Da were detected (see FIG. 7A). It was found that these three peaks corresponded to the peptide segment having a molecular weight of 3660.3, by deconvolution analysis. They were the tetravalent, trivalent, and divalent ions of said peptide segments, respectively. And, the peptide segment consisting of VIGGDECDINEHPF and GAITTSEDTYPDVPHCANIN linked via disulfide bond just had a molecular weight of 3660.9 Da. Therefore, it could be deduced that these two peptide segments were linked via the disulfide bond. Further second mass spectrum data could verify this deduction. FIG. 7B shows the second mass spectrum of VIGGDECDINEHPF and GAITTSEDTYPDVPHCANIN linked via a disulfide bond. In the experiments, a series of $C^{139}$-y2 ions ($Cys^{139}$-y2-5 to $Cys^{139}$-y2-18) were detected. These results sufficiently confirmed the presence of the disulfide bond. For example, the charge mass ratio of $Cys^{139}$-y2-10 was 1311.33 Da. $C^{139}$ indicated that the ion was produced by disruption of the peptide chain containing $Cys^{139}$ residue, while the other peptide chain was still linked thereto via the disulfide bond. The y2 indicated that the ion was an ion of y2 series, which carried 2 charges. 10 represented the position (Y-P) where the peptide bond was disrupted.

The results showed that the rate of correct match of disulfide bond in rBAT in the prepared rBAT stock solution was ≧95%.

3.4 rBAT Stock Solution I Obtained after Fermentation, Chromatography, and Purification:
Purification: 98%
Concentration: 1.02 mg/ml
Specific Activity: 2000 KU/mg.

EXAMPLE 3

Examples Studying the Purification Processes

1. Study on the Conditions of Hydrophobic Chromatography

Since the fermentation used an inorganic salt media (pH ~6.0), the fermentation supernatant contained salts in a relatively high concentration and the electric conductivity was also relatively high. Therefore, the hydrophobic chromatography was used as the first step for purification to crudely purify rBAT.

1.1 Study on the Conditions of Hydrophobic Chromatography when pH was 6.0

Each 100 ml of the fermentation supernatant was subjected to the following processes:

|  | Volume of fermentation supernatant (ml) | Volume of 3M ammonium sulfate (ml) | Volume of water for injection (ml) | Total volume (ml) | Concentration of ammonium sulfate (M) |
|---|---|---|---|---|---|
| Group A | 100 | 150 | 50 | 300 | 1.5 |
| Group B | 100 | 100 | 100 | 300 | 1.0 |
| Group C | 100 | 50 | 150 | 300 | 0.5 |

After the pH value was adjusted to 6.0, the above groups A, B and C were centrifugated at 12000 rpm for 10 minutes under room temperature. The supernatants were collected for detecting the activity, respectively.

The Phenyl Sepharose Fast Flow (1 ml) was selected and pre-packaged in the column.

After equilibrium with buffer 1 (20 mM PB, 1.5M $(NH_4)_2SO_4$, pH 6.0), group A solution was loaded (the loaded volume was 100 ml which was same hereinafter). The effluent liquid was collected for detecting activity. After regeneration of the Phenyl Sepharose FastFlow (1 ml pre-packaged column) and equilibrium with buffer 2 (20 mM to PB, 1.0M $(NH_4)_2SO_4$, pH 6.0), group B solution was loaded. The effluent liquid was collected for detecting activity. After regeneration of the Phenyl Sepharose FastFlow (1 ml pre-packaged column) and equilibrium with buffer 3 (20 mM PB, 0.5M $(NH_4)_2SO_4$, pH 6.0), group C solution was loaded. The effluent liquid was collected for detecting activity. The results were shown in the table below.

|  | Fermentation supernatant | A | B | C |
|---|---|---|---|---|
| Activity of the loading solution (KU/ml) | 10 | 3 | 3 | 3 |
| Activity of the effluent liquid (KU/ml) |  | 1 | 1 | 2 |

From the data in the above table, it could be found that under said conditions rBAT poorly bond to Phenyl Sepharose Fast Flow. A significant amount of rBAT was outflowed. Therefore, these conditions were not suitable for purifying rBAT.

1.2 Study on the Conditions of Hydrophobic Chromatography when pH was 5.0

Each of 100 ml of the fermentation supernatant was subjected to the following processes:

|  | Volume of fermentation supernatant (ml) | Volume of 3M ammonium sulfate (ml) | Volume of water for injection (ml) | Total volume (ml) | Concentration of ammonium sulfate (M) |
|---|---|---|---|---|---|
| Group D | 100 | 150 | 50 | 300 | 1.5 |
| Group E | 100 | 100 | 100 | 300 | 1.0 |
| Group F | 100 | 50 | 150 | 300 | 0.5 |

After the pH value was adjusted to 5.0, the above groups D, E and F were centrifugated at 12000 rpm for 10 minutes under room temperature. The supernatants were collected for detecting the activity, respectively.

The Phenyl Sepharose Fast Flow (1 ml) was selected and pre-packaged in the column. After equilibrium with buffer 4 (20 mM NaAc—HAc, 1.5M $(NH_4)_2SO_4$, pH 5.0), group D solution was loaded (the loaded volume was 100 ml which was same hereinafter). The effluent liquid was collected for detecting activity. After regeneration of the Phenyl Sepharose FastFlow (1 ml pre-packaged column) and equilibrium with buffer 5 (20 mM NaAc—HAc, 11.0M $NH_4)_2SO_4$, pH 5.0), group E solution was loaded. The effluent liquid was collected for detecting activity. After regeneration of the Phenyl Sepharose FastFlow (1 ml pre-packaged column) and equilibrium with buffer 6 (20 mM NaAc—HAc, 0.5M$(NH_4)_2SO_4$, pH 5.0), group F solution was loaded. The effluent liquid was collected for detecting activity. The results were shown in the table below.

|  | Fermentation supernatant | D | E | F |
|---|---|---|---|---|
| Activity of the loading solution (KU/ml) | 10 | 3 | 3 | 3 |
| Activity of the effluent solution (KU/ml) |  | 1 | 1 | 2 |

After the pH value was lowered, the hydrophobicity of rBAT was slightly increased. As compared with pH 6.0, the activity of the effluent liquid was not changed significantly. There were still a considerable amount of rBAT outflowed. Therefore, the hydrophobic fillers should be changed for further study.

1.3 Study on Butyl and Octyl Fillers when pH was 5.0

Each of 100 ml of the fermentation supernatant was subjected to the following processes:

|  | Volume of fermentation supernatant (ml) | Volume of 3M ammonium sulfate (ml) | Volume of water for injection (ml) | Total volume (ml) | Concentration of ammonium sulfate (M) |
|---|---|---|---|---|---|
| Group G | 100 | 150 | 50 | 300 | 1.5 |
| Group H | 100 | 150 | 50 | 300 | 1.5 |

After the pH value was adjusted to 5.0, the above groups G and H were centrifugated at 12000 rpm for 10 minutes under room temperature. The supernatants were collected for detecting the activity, respectively.

The Butyl Sepharose Fast Flow (1 ml) was selected and pre-packaged in the column. After equilibrium with buffer 7 (20 mM NaAc—HAc, 1.5M$(NH_4)_2SO_4$, pH 5.0), group G solution was loaded (the loaded volume was 100 ml, which was same hereinafter). The effluent liquid was collected for detecting activity. The Octyl Sepharose FastFlow (1 ml pre-packaged column) was used. After equilibrium with buffer 8 (20 mM NaAc—HAc, 1.5M$(NH_4)_2SO_4$, pH 5.0), group H solution was loaded. The effluent liquid was collected for detecting activity. The results were shown in the table below.

|  | Fermentation supernatant | G | H |
|---|---|---|---|
| Activity of the loading solution (KU/ml) | 10 | 3 | 3 |
| Activity of the effluent solution (KU/ml) |  | 1 | 1 |

Under these conditions, the binding between rBAT and the fillers was not improved. There was still a high ratio of rBAT in the effluent solution.

In summary, we deemed that hydrophobic chromatography is not suitable for purifying rBAT protein for the following reasons: the binding property between rBAT and hydrophobic media was poor, so, even if the pH of the whole operating system is lowered, the improvement is not significant. Moreover, the above operations were performed under room temperature, if the operating temperature was increased to improve the hydrophobicity, the activity of the rBAT protein might be influenced.

2. Study on Cation-Exchange Chromatography

Since there were a lot of protein impurities, inorganic salts, pigments and the like in the fermentation supernatant, it was intended to adopt ultrafiltration to desalt, remove the protein impurities and replace the buffer, so as to facilitate the subsequent ion-exchange chromatography. However, since it was unclear which buffer would be suitable for ion-exchange chromatography for the rBAT protein, that is, it was unclear which buffer should be replaced during ultrafiltration, it should first study the adsorption behavior of the rBAT protein in the ion-exchange chromatography under different conditions, so as to determine the buffer and then study the conditions for ultrafiltration.

2.1 Optimal pH and Preferred Electric Conductivity of the Loading Samples

The pH of the fermentation supernatant was adjusted with 1M HAc to 4.5, 5.0, 5.5, and 6.0, respectively, according to the isoelectric point of rBAT (the theoretical isoelectric point was 7.39). Under each pH value, the fermentation supernatants were diluted with water for injection to the electrical conductivity as indicated in the table below. The 1 ml SP Sepharose Fast Flow pre-packaged column was used. The loading volume was 50 ml of fermentation supernatant (before dilution). The flow rate was 11.0 ml/min. The effluent liquid was collected from detecting activity, so as to optimize the conditions for the loading solution. The results were shown below.

pH 4.5, the equilibrium buffer was 20 mM NaAc—HAc, pH 4.5

| Electrical conductance of loading solution (mS/cm) | 4.0 | 8.0 | 12.0 | 16.0 |
|---|---|---|---|---|
| Times of diluting fermentation solution | 12 | 6 | 4 | 3 |
| Time of blood coagulation | coagulation after 100 seconds | coagulation after 35 seconds | coagulation after 22 seconds | coagulation after 16 seconds |
| Time of blood coagulation | No coagulation after 10 minutes | coagulation after 305 seconds | coagulation after 125 seconds | coagulation after 75 seconds | pH=5.0, the equilibrium buffer was 20 mM NaAc—HAc, pH 5.0

| Electrical conductance of the loading solution (mS/cm) | 4.0 | 8.0 | 12.0 | 16.0 |
|---|---|---|---|---|
| Times of diluting fermentation solution | 12 | 6 | 4 | 3 |
| Time of blood coagulation | coagulation after 98 seconds | coagulation after 35 seconds | coagulation after 23 seconds | coagulation after 15 seconds |
| Time of blood coagulation | No coagulation after 10 minutes | coagulation after 280 seconds | coagulation after 108 seconds | coagulation after 64 seconds | pH=5.5, the equilibrium buffer was 20 mM NaAc—HAc, pH 5.5

| Electrical conductance of the loading solution (mS/cm) | 4.0 | 8.0 | 12.0 | 16.0 |
|---|---|---|---|---|
| Times of diluting fermentation solution | 12 | 6 | 4 | 3 |
| Time of blood coagulation | coagulation after 98 seconds | coagulation after 36 seconds | coagulation after 25 seconds | coagulation after 15 seconds |
| Time of blood coagulation | coagulation after 450 seconds | coagulation after 265 seconds | coagulation after 85 seconds | coagulation after 56 seconds | pH=6.0, the equilibrium buffer was 20 mM NaAc—HAc, pH 6.0

| Electric conductivity of loading solution (mS/cm) | 4.0 | 8.0 | 12.0 | 16.0 |
|---|---|---|---|---|
| Times of diluting fermentation solution | 12 | 6 | 4 | 3 |
| Time of blood coagulation | coagulation after 120 seconds | coagulation after 36 seconds | coagulation after 25 seconds | coagulation after 16 seconds |
| Time of blood coagulation | coagulation after 380 seconds | coagulation after 240 seconds | coagulation after 63 seconds | coagulation after 48 seconds |

From the data in the above tables, it could be known that under pH 4.5 and 5.0, and 4.0 mS/cm of electric conductivity of the dilutions, rBAT was not basically outflowed. Considering the effect of the pH on the rBAT protein activity, the following conditions were selected to study the elution behavior of the rBAT protein in cation-exchange chromatography: pH 5.0 of the fermentation supernatant 5.0, 4.0 mS/cm of the electrical conductance of the dilution, and equilibrium buffer of 20 mM NaAc—HAc, pH 5.0. Therefore, the buffer replaced during ultrafiltration was 20 mM NaAc—HAc, pH 5.0, and the ultrafiltration should be performed until the electrical conductance was below 4.0 mS/cm.

2.2 Study on the Conditions of Ultrafiltration

Millipore Pellicon 10K ultrafiltration apparatus, and Millipore Masterflex peristatic pump were used. The operating parameters were as follows: the input pressure and output pressure of the ultrafiltration instrument were controlled to be 10 psi and 5 psi, respectively. The flow rate was 200 ml/min. After equilibrium of the ultrafiltration apparatus successively with water for injection and buffer of 20 mM NaAc—HAc (pH 5.0), 5 L of the fermentation solution were subjected to ultrafiltration. When 1 L of the fermentation solution was remained, a buffer of 20 mM NaAc—HAc, pH 5.0 was added to a volume of 5 L (repeated 3 times). And then a buffer of 20 mM NaAc—HAc, pH 5.0 was added to a volume of 5 L (after determination, pH was 5.0, and the electrical conductance was 3.5 mS/cm), and the fermentation solution, ultrafiltration solution and the effluent liquid were sampled for detecting activity. The results were shown as follows.

|  | Fermentation solution | Ultrafiltration solution | Effluent liquid |
|---|---|---|---|
| Volume (L) | 5 | 5 | 12 |
| Activity (KU/ml) | 10 | 8 | coagulation after 150 seconds |

The loss under these conditions for ultrafiltration was about 20%, which may result from the non-specific absorption of the membrane stack or the large operating pressure. Therefore, when performing the second experiment, the input pressure and output pressure were adjusted with water for injection to 6 psi and 3 psi, respectively, and the flow rate was adjusted to be 120 ml/min. A buffer of 20 mM NaAc—HAc, 0.15M NaCl, pH 5.0 was used to balance the ultrafiltration system. 5 L of fermentation solution were subjected to ultrafiltration. When 1 L of the fermentation solution was remained, a buffer of 20 mM NaAc—HAc, pH 5.0 was added to 5 L of volume (repeated 3 times). And then a buffer of 20 mM NaAc—HAc, pH 5.0 was added to a volume of 5 L (after determination, pH was 5.0, and the electrical conductance was 3.5 mS/cm), and the fermentation solution, ultrafiltration solution and the effluent liquid were sampled for detecting activity. The results were shown as follows.

|  | Fermentation solution | Ultrafiltration solution | Effluent liquid |
|---|---|---|---|
| Volume (L) | 5 | 5 | 12 |
| Activity (KU/ml) | 10 | 9 | coagulation after 10 minutes |

The results showed that the yield of activity of rBAT was above 90% by ultrafiltration to replace the buffer. The fermentation supernatant obtained after ultrafiltration was favorable to the subsequent cation-exchange chromatography.

2.3 Study on the Elution Conditions of Cation-Exchange Chromatography

The 1 ml SP Sepharose F F pre-packaged column was used. The equilibrium buffer A was 20 mM NaAc—HAc, pH 5.0, the elution buffer B was 20 mM NaAc—Hac, 1.0M NaCl, pH 5.0. 50 ml of fermentation supernatant obtained after ultrafiltration were loaded in a rate of 11.0 ml/min. After loading, equilibrium buffer A was used for equilibrium. A gradient elution was performed under the conditions of 0-100% B, 20 CV, and a flow rate of 1.0 ml/min. It was found that, during the elution with 0-100% B, three elution peaks were obtained, which were present at 18% B, 45% B and 60% B, respectively. Samples were obtained respectively for detecting activity. Finally, 2M NaCl was used to regenerate the column and the regeneration peak was collected for detecting activity. All results were shown below.

|  | Forepart of the 18% peak | Middle part of the 18% peak | Posterior segment of the 18% peak | Forepart of the 45% peak | Middle part of the 45% peak |
|---|---|---|---|---|---|
| Activity (KU/ml) | No coagulation after 10 minutes | 1 | 10 | 40 | 300 |
|  | Posterior segment of the 45% peak | Forepart of the 60% peak | Middle part of the 60% peak | Posterior segment of the 60% peak | 2M regeneration peak |
| Activity (KU/ml) | 50 | 8 | 125 seconds | No coagulation after 10 minutes | No coagulation after 10 minutes |

From the data in the above table, rBAT protein was mainly concentrated in the 45% B (0.45M NaCl) elution peak. However, in the middle and posterior segments of the 18% B (0.18M NaCl) elution peak, and in the forepart and middle part of the 60% B (0.60M NaCl) elution peak, there was a small amount of rBAT protein. Therefore, the 18% B should be suitably lowered and the 45% B should be suitably increased, so as to concentrate the rBAT protein mainly in one elution peak. Therefore, the above experimental processes were repeated, with exception that 15% B, 50% B and 100% B were used for elution by stages. Each elution peak was respectively collected for detecting activity. The results were shown as follows.

|  | Forepart of the 15% peak | Middle part of the 15% peak | Posterior segment of the 15% peak | Forepart of the 50% peak | Middle part of the 50% peak |
|---|---|---|---|---|---|
| Activity (KU/ml) | No coagulation after 10 minutes | No coagulation after 10 minutes | coagulation after 135 seconds | 50 | 320 |
|  | Posterior segment of the 10% peak | Forepart of the 100% peak | Middle part of the 100% peak | Posterior segment of the 100% peak | 2M regeneration peak |
| Activity (KU/ml) | 65 | coagulation after 114 seconds | No coagulation after 10 minutes | No coagulation after 10 minutes | No coagulation after 10 minutes |

From the data in the above table, it showed that most of rBAT protein was concentrated in the 50% B (0.5M NaCl) elution peak. Although there was a little amount of rBAT protein in the posterior segment of the 15% B (0.15M NaCl) elution peak and the forepart of the 100% B (11.0M NaCl) elution peak, the activity was very low as compared with the fermentation solution. Therefore, the elution conditions were eventually determined as 20 mM NaAc—HAc, 0.15M NaCl, pH 5.0; 20 mM NaAc—HAc, 0.50M NaCl, pH 5.0; and 20 mM NaAc—HAc, 11.0M NaCl, pH 5.0; and the elution peak of 20 mM NaAc—HAc, 0.50M NaCl, pH 5.0 was collected, which was the rBAT protein peak.

2.4 Study on the Course of Cation-Exchange Chromatography

The chromatography column of 1.6×15 cm was used, which was filled with 20 ml SP Sepharose FF. The flow rate of loading was 10 ml/min. 1000 ml of the fermentation supernatant obtained after ultrafiltration was loaded. The equilibrium buffer was 20 mM NaAc—HAc, pH 5.0, the elution buffers were 20 mM NaAc—HAc, 0.15M NaCl, pH 5.0; 20 mM NaAc—HAc, 0.50M NaCl, pH 5.0; and 20 mM NaAc—HAc, 11.0M NaCl, pH 5.0, respectively. Each elution peak was collected (the 11.0M elution peak had a large amount of pigments). The elution maps and electrophoresis maps were indicated in FIG. 14.

Each collection solution was sampled for detecting activity. The results were shown as follows.

|  | Fermentation solution | 0.15M Elution peak | 0.50M Elution peak | 1.0M Elution peak |
| --- | --- | --- | --- | --- |
| Activity (KU/ml) | 10 | No coagulation after 10 minutes | 230 | No coagulation after 10 minutes |

The results showed that the elution peak obtained from 20 mM NaAc—HAc, 0.50M NaCl, pH 5.0 was the rBAT protein peak.

3. Study on the Anion-Exchange Chromatography 3.1 Optimal pH and Preferred Electrical Conductance of the Loading Solution The pH of the elution peak obtained from 20 mM NaAc—HAc, 0.50M NaCl, pH 5.0 in the previous step was adjusted with 1M NaOH to 8.0, 8.5, and 9.0, respectively, according to the isoelectric point of rBAT (the theoretical isoelectric point was 7.39). Under each pH value, the solutions were diluted with water for injection to the electrical conductance as indicated in the table below. The 1 ml Q Sepharose Fast Flow pre-packaged column was used. The loading volume was 10 ml of the rBAT collection solution obtained from the cation-exchange (before dilution). The flow rate was 11.0 ml/min. The effluent liquid was collected from detecting activity, so as to optimize the conditions for the loading solution. The results were shown below.

pH=8.0, the equilibrium buffer was 20 mM Tris-HCl, pH 8.0

| Electrical conductance of the loading solution (mS/cm) | 3.0 | 6.0 | 9.0 | 12.0 |
| --- | --- | --- | --- | --- |
| Times of dilution | 15 | 8 | 5 | 4 |
| Activity of the loading solution (KU/ml) | 15 | 28 | 44 | 55 |
| Activity of the effluent liquid (KU/ml) | 1 | 5 | 16 | 27 | pH=8.5, the equilibrium buffer was 20 mM Tris-HCl, pH 8.5

| Electrical conductance of the loading solution (mS/cm) | 3.0 | 6.0 | 9.0 | 12.0 |
| --- | --- | --- | --- | --- |
| Times of dilution | 15 | 8 | 5 | 4 |
| Activity of the loading solution (KU/ml) | 15 | 28 | 43 | 54 |
| Activity of the effluent liquid (KU/ml) | coagulation after 275 minutes | 3 | 14 | 25 | pH=9.0, the equilibrium buffer was 20 mM Tris-HCl, pH 9.0

| Electrical conductance of the loading solution (mS/cm) | 3.0 | 6.0 | 9.0 | 12.0 |
| --- | --- | --- | --- | --- |
| Times of dilution | 15 | 8 | 5 | 4 |
| Activity of the loading solution (KU/ml) | 14 | 27 | 41 | 52 |
| Activity of the effluent liquid (KU/ml) | No coagulation after 10 minutes | 1 | 10 | 21 |

From the data in the above table, it was known that when pH=9.0, and the electrical conductance of the diluted solution was 3.0 mS/cm, almost no rBAT was outflowed. Therefore, the following conditions were selected for studying the elution conditions of the anion-exchange chromatography for rBAT protein: the pH of the rBAT collection solution obtained from the cation-exchange was adjusted to 9.0, the electric conductivity of the diluted solution was adjusted to 3.0 mS/cm, and the equilibrium buffer was 20 mM Tris-HCl, pH 9.0.

3.2 Study on the Elution Conditions of the Anion-Exchange Chromatography

The 1 ml Q Sepharose Fast Flow pre-packaged column was used. The equilibrium buffer A was 20 mM Tris-HCl, pH 9.0, the elution buffer B was 20 mM Tris-HCl, 11.0M NaCl, pH 9.0. The pH value of 10 ml of the rBAT collection solution obtained from the cation-exchange was adjusted to 9.0, and the electric conductivity of the diluted solution was adjusted to 3.0 mS/cm, and then the sample was loaded in a rate of 11.0 ml/min. A gradient elution was firstly performed under the conditions of 0-100% B, 20 CV, and a flow rate of 11.0 ml/min. It was found that, during the elution with 0-100% B, two elution peaks were obtained, which were present at 10% B and 50% B, respectively. However, the 10% B peak had relatively serious conditions of streaking. Samples were obtained respectively for detecting activity. Finally, 2M NaCl was used to regenerate the column and the regeneration peak was collected for detecting activity. All results were shown below.

|  | 0.10M elution peak | Tail of the 0.10M elution peak | 0.50M elution peak | 2M regeneration peak |
| --- | --- | --- | --- | --- |
| Activity (KU/ml) | 800 | 50 | 10 | No coagulation after 10 minutes |

To overcome the streaking phenomena in the 10% B elution peak, the elution conditions were changed into 0-40% B, 5 CV, and then increased to 50% B. The flow rate was 10 ml/min. The streaking of the first peak was significantly reduced. The peak spike was at 15% B. Samples were obtained respectively for detecting activity. The results were shown below.

|  | 0.15M elution peak | Tail of the 0.15M elution peak | 0.50M elution peak | 2M regeneration peak |
|---|---|---|---|---|
| Activity (KU/ml) | 1100 | 30 | 2 | No coagulation after 10 minutes |

Therefore, the elution conditions were finally determined as 20 mM Tris-HCl, 0.15M NaCl, pH 9.0, and 20 mM Tris-HCl, 0.50M NaCl, pH 9.0. The protein elution peak obtained from 20 mM Tris-HCl, 0.15M NaCl, pH 9.0 was the rBAT protein peak.

3.3 Study on the Course of the Anion-Exchange Chromatography

The chromatography column of 1.6×15 cm was used, which was filled with 20 ml Q Sephrose Fast Flow. The flow rate of loading was 10 ml/min. The pH of 200 ml of the rBAT collection solution obtained from the cation-exchange was adjusted to 9.0 and the electric conductivity of the diluted solution was adjusted to 300 mS/cm and then the sample was loaded. The equilibrium buffer was 20 mM Tris-HCl, pH 9.0, the elution buffers were 20 mM Tris-HCl, 0.15M NaCl, pH 9.0, and 20 mM Tris-HCl, 0.50M NaCl, pH 9.0, respectively. Each elution peak was collected. The elution map and electrophoresis analysis (non-reduced SDS-PAGE) were indicated in FIG. 15.

Each collected solution was sampled for detecting activity. The results were shown as follows.

|  | The loading solution | 0.15M elution peak | 0.50M elution peak |
|---|---|---|---|
| Activity (KU/ml) | 15 | 1060 | 3 |

It was shown that the elution peak obtained from 20 mM Tris-HCl, 0.15M NaCl, pH 9.0 was the rBAT protein peak.

4. Conditions of Gel Filtration Chromatography

The Superdex 75 fillers of Pharmacia Company and the 6.0×60 cm pre-packaged column, CV1700 ml were used. The equilibrium buffer was 20 mM NaAc—HAc, 0.15M NaCl, pH 5.0. The eluate of 20 mM Tris-HCl, 0.15M NaCl, pH 9.0 obtained in the anion-exchange chromatography was loaded in batch, with each batch no more than 85 ml (5% of the column volume). The elution peaks were collected in stages. The samples with purity higher than 95% were pooled and sterilized, thus obtaining the rBAT stock solution.

The elution map and electrophoresis map were shown in FIG. 16.

5. Study on the Repeatability of the Purification Process

A batch of the fermentation supernatant obtained by the method of Example 1 were subjected to the following processes for three times for validating the purification process. The results were shown as follows.

| Fermentation solution | Volume of the fermentation supernatant (ml) | 4000 | 4000 | 4000 |
|---|---|---|---|---|
|  | Activity (KU/ml) | 10 | 10 | 10 |
| Gel filtration | Elution volume of gel filtration (ml) | 38 | 35 | 33 |
|  | Content of rBAT (mg/ml) | 0.87 | 1.05 | 0.95 |
|  | Activity (KU/ml) | 348 | 405 | 390 |
|  | Total yield (%) | 33.1 | 35.4 | 32.2 |

* The average total yield was 33.6%.

6. Pilot Scale Experiment of the Purification Process 6.1 Replacement of buffer by ultrafiltration. Millipore Pellicon 10K ultrafiltration membrane stack, and Millipore Masterflex peristatic pump were used. The input pressure and output pressure of the ultrafiltration instrument were controlled to be 6 psi and 3 psi, respectively. The flow rate was 120 ml/min. After equilibrium of the ultrafiltration membrane successively with water for injection and buffer of 20 mM NaAc—HAc+0.15M NaCl (pH 5.0), the fermentation supernatant was subjected to ultrafiltration. During ultrafiltration, when the volume of the solution reached ⅕ of the original volume, buffer of 20 mM NaAc—HAc (pH 5.0) was added to the original volume (repeated three times). And then a buffer of 20 mM NaAc—HAc (pH 5.0) was added to the original volume and the resulted solution was used as a loading solution for the cation-exchange chromatography.

6.2: Cation-exchange chromatography. The fermentation supernatant obtained after ultrafiltration was loaded to a SP Sepharose Fast Flow for performing cation-exchange chromatography. The column was in a gauge of Index 70/500 mm, 7.5 cm of the height of layer and 300 ml of the bed volume of the column. The equilibrium buffer was 20 mM NaAc—HAc (pH 5.0), the elution buffers were 20 mM NaAc—HAc, 0.15M NaCl (pH 5.0), 20 mM NaAc—HAc, 0.50M NaCl (pH 5.0), and 20 mM NaAc—HAc, 1.0M NaCl (pH 4.0), respectively. The elution peak of 20 mM NaAc—HAc, 0.50M NaCl (pH 5.0) was collected.

6.3: Anion-exchange chromatography. The pH of the eluate of 20 mM NaAc—HAc, 0.50M NaCl (pH 5.0) obtained from the cation-exchange chromatography was adjusted to 9.0, and the eluate was diluted so that the electric conductivity was below 3.0 mS/cm, and then the sample was loaded onto a Q Sepharose Fast Flow for anion-exchange chromatography, which had a gauge of 36/60, 6 cm of height of layer, and 60 ml of the bed volume of the column. The equilibrium buffer was 20 mM Tris-HCl (pH 9.0), the elution buffers were 20 mM Tris-HCl, 0.15M NaCl (pH 9.0), and 20 mM Tris-HCl, 0.50M NaCl (pH 9.0), respectively. The eluate of 20 mM Tris-HCl, 0.15M NaCl (pH 9.0) was collected.

6.4: Gel filtration chromatography. The eluate of 20 mM Tris-HCl, 0.15M NaCl (pH 9.0) from the anion-exchange chromatography was loaded in batch onto the molecular sieve Superdex 75, which had a gauge of 60/600 mm pre-packaged column, 1700 ml of bed volume. The amount for each loading was not more than 5% of the bed volume (85 ml). The buffer was 20 mM NaAc—HAc, 0.15M NaCl (pH 5.0). The eluates were collected in stages and the samples with a purity of higher than 95% were pooled and sterilized to obtain the rBAT stock solution 1.

6.5 The purification results obtained from three batches of the pilot scale experiment were shown in the following table.

| Item | Volume (ml) | Content of Protein (mg/ml) | rBAT Purity (%) | Activity (KU/ml) | Activity (KU/mg) | Yield of Activity (%) |
|---|---|---|---|---|---|---|
| Batch Number: 20030601 | | | | | | |
| Fermentation supernatant | 12500 | | 5 | 10 | | |
| Supernatant after ultrafiltration | 12500 | | 6 | 9 | | 90 |
| SP Sepharose FF | 392 | 1.43 | 38 | 235 | 164.3 | 81.9 |
| Q Sepharose FF | 72 | 3.66 | 68 | 1022 | 279.2 | 79.9 |
| Superdex 75 | 126 | 0.75 | 98.1 | 320 | 426.7 | 54.8 |
| Total yield | | | 90% × 81.9% × 79.9% × 54.8% = 32.3% | | | |
| Batch Number: 20030602 | | | | | | |
| Fermentation supernatant | 12200 | | 6 | 11 | | |
| Supernatant after ultrafiltration | 12500 | | 7.5 | 10 | | 93.1 |
| SP Sepharose FF | 412 | 1.82 | 40 | 262 | 144.0 | 86.3 |
| Q Sepharose FF | 75 | 4.17 | 72 | 1116 | 267.6 | 77.5 |
| Superdex 75 | 152 | 0.83 | 98.7 | 320 | 385.5 | 58.1 |
| Total yield | | | 93.1% × 86.3% × 77.5% × 58.1% = 36.2% | | | |
| Batch Number: 20030603 | | | | | | |
| Fermentation supernatant | 12300 | | 5.5 | 11 | | |
| Supernatant after ultrafiltration | 12500 | | 7 | 10 | | 92.4 |
| SP Sepharose FF | 405 | 1.70 | 43 | 256 | 150.6 | 82.9 |
| Q Sepharose FF | 76 | 3.75 | 70 | 1007 | 268.5 | 73.8 |
| Superdex 75 | 137 | 0.79 | 98.5 | 320 | 405.1 | 57.3 |
| Total yield | | | 92.4% × 82.9% × 73.8% × 57.3% = 32.4% | | | |

EXAMPLES 4-10

Pharmaceutical Composition

The highly purified recombinant batroxobin obtained in Example 1 (the rBAT stock solution 1) was mixed with the water for injection containing the pharmaceutical excipients as shown in the below table, thereby obtaining a formulation of the recombinant batroxobin.

| | formulation | | | | | | |
|---|---|---|---|---|---|---|---|
| Components | Example 4 | Example 5 | Example 6 | Example 7 | Example 8 | Example 9 | Example 10 |
| Sodium phosphate buffer, 20 mM pH 6.0 | ✓ | ✓ | ✓ | ✓ | ✓ | ✓ | ✓ |
| Sodium chloride, 0.85% | ✓ | ✓ | ✓ | ✓ | ✓ | ✓ | ✓ |
| L-glutathione, 0.0001 mM | ✓ | ✓ | ✓ | ✓ | ✓ | ✓ | ✓ |
| hydrolyzed gelatin, 1 mg/ml | ✓ | — | — | — | — | — | — |
| Glycine, 5% | — | ✓ | — | — | — | — | — |
| Trehalose, 5% | — | — | ✓ | — | — | — | — |
| hydrolyzed gelatin, 0.1 mg/ml | — | — | — | ✓ | — | — | — |
| hydrolyzed gelatin, 2 mg/ml | — | — | — | — | ✓ | — | ✓ |
| Glycine, 3.4% | — | — | — | — | — | ✓ | — |
| trichloro butyl alcohol, 3 mg/ml | — | — | — | — | — | — | ✓ |

✓ represents that the formulation contains the indicated component.

EXAMPLES 11-17

Examples on Stability Determination

The formulations were those prepared in Examples 4-10. Experimental Results of 37° C. Stability Test The recombinant batroxocin formulations of Examples 4-10 were all 1 KU/ml, which means that, in each detection point, 100 μl solution of certain formulation containing the recombinant batroxocin was mixed with the human standard plasma which had been subjected to the anticoagulation treatment, and coagulation could be obtained within 60±20 seconds under 37° C. The formulations whose coagulation time went beyond this scope were not qualified.

When performing the stability test for the formulations, the stock solution was diluted so that the activity concentration was 1 KU/ml.

The recombinant batroxocin formulations of Examples 4-10 were stored under 37° C., and the blood coagulation times (second) were detected in each detection point. The results were shown as follows.

| formulation | Time (day) | | | | | | | | | |
|---|---|---|---|---|---|---|---|---|---|---|
| | 0 | 7 | 14 | 21 | 28 | 60 | 90 | 120 | 150 | 180 |
| Example 4 | 69.6 | 71.8 | 74.2 | 80 | 75.1 | 75.0 | 73.8 | 76.4 | 81.7 | 82.0 |
| Example 5 | 52.0 | 100.2 | — | — | — | — | — | — | — | — |
| Example 6 | 67 | 92.5 | — | — | — | — | — | — | — | — |
| Example 7 | 71.1 | 99.2 | — | — | — | — | — | — | — | — |
| Example 8 | 67.7 | 70.2 | 71.8 | 73.7 | 69.4 | 67.8 | 68.7 | 68.9 | 72.4 | 73.7 |
| Example 9 | 57.0 | 103.6 | — | — | — | — | — | — | — | — |
| Example 10 | 45.2 | 61.9 | 65.6 | 69 | 70 | 71 | 73 | 70 | 73 | 69 |
| All blanks | | | | | >196 | | | | | |

>196 s indicates that no blood coagulation occurs even going beyond the maximal range of the coagulometer.

The results showed that use of the hydrolyzed gelatin as a protection agent might make the recombinant batroxobin having a relatively high stability and it could be stable for 100 days under 37° C.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

---

What is claimed is:

1. A purified recombinant batroxobin product, wherein the product consists of purified recombinant batroxobin, the batroxobin having the following properties:
(a) the batroxobin has a molecular weight of 29-32 kDa;
(b) positions 146 and 225 in SEQ ID NO:1 are N-glycosylated; and
(c) the specific activity of the batroxobin is in a range of 1500-3000 KU/mg protein, wherein at least 90% of the purified recombinant batroxobin included in the product have 6 pairs of disulfide bonds which correctly match at $Cys^7$-$Cys^{139}$, $Cys^{26}$-$Cys^{42}$, $Cys^{74}$-$Cys^{230}$, $Cys^{118}$-$Cys^{184}$, $Cys^{150}$-$Cys^{163}$ and $Cys^{174}$-$Cys^{199}$.

2. The product of claim 1, wherein at least 95% of the recombinant batroxobin have 6 pairs of disulfide bonds which correctly match.

3. The product of claim 1, wherein the batroxobin is N-glycosylated at at least one Asn residue in the following sites: $Asn^{146}$-$Asn^{147}$-$Thr^{148}$ and $Asn^{225}$-$Lys^{226}$-$Thr^{228}$.

4. The product of claim 1, wherein the N-glycosylation adds 4000-6000 Da to the molecular weight of the batroxobin protein on the basis of 25.6 kDa.

5. The product of claim 1, wherein at least 99% of the batroxobin have 6 pairs of disulfide bonds which correctly match.

6. A method of hemostasis, comprising: administering a subject in need thereof the product of claim 1.

7. A pharmaceutical composition, which comprises the product of claim 1 and a pharmaceutically acceptable carrier.

8. The composition of claim 7, further comprising a hydrolyzed gelatin as a stabilizer.

9. The composition of claim 7, wherein said composition is a liquid or a freeze-dried powder.

* * * * *

UNITED STATES PATENT AND TRADEMARK OFFICE
CERTIFICATE OF CORRECTION

| | | |
|---|---|---|
| PATENT NO. | : 7,939,067 B2 | Page 1 of 1 |
| APPLICATION NO. | : 12/568234 | |
| DATED | : May 10, 2011 | |
| INVENTOR(S) | : Huang et al. | |

It is certified that error appears in the above-identified patent and that said Letters Patent is hereby corrected as shown below:

Column 2, line 5: "an" should read --a--.
Column 4, line 1: "shows" should read --show--.
Column 4, line 8: "shows" should read --show--.
Column 4, line 32: "11.0" should read --1.0--.
Column 13, line 21: "11.0" should read --1.0--.
Column 14, line 67: "11.0" should read --1.0--.
Column 18, line 7: "11.0" should read --1.0--.
Column 19, line 5: "11.0" should read --1.0--.
Column 19, line 10: "11.0" should read --1.0--.
Column 19, line 22: "11.0" should read --1.0--.
Column 19, line 23: "11.0" should read --1.0--.
Column 19, line 51: "11.0" should read --1.0--.
Column 20, line 40: "11.0" should read --1.0--.
Column 20, line 44: "11.0" should read --1.0--.
Column 20, line 46: "11.0" should read --1.0--.
Column 20, line 67: "10" should read --1.0--.

Signed and Sealed this
Twenty-seventh Day of December, 2011

David J. Kappos
*Director of the United States Patent and Trademark Office*

SEQUENCE LISTING

<160> NUMBER OF SEQ ID NOS: 5

<210> SEQ ID NO 1
<211> LENGTH: 231
<212> TYPE: PRT
<213> ORGANISM: Bothrops atrox

<400> SEQUENCE: 1

```
Val Ile Gly Gly Asp Glu Cys Asp Ile Asn Glu His Pro Phe Leu Ala
1               5                   10                  15

Phe Met Tyr Tyr Ser Pro Arg Tyr Phe Cys Gly Met Thr Leu Ile Asn
            20                  25                  30

Gln Glu Trp Val Leu Thr Ala Ala His Cys Asn Arg Arg Phe Met Arg
        35                  40                  45

Ile His Leu Gly Lys His Ala Gly Ser Val Ala Asn Tyr Asp Glu Val
    50                  55                  60

Val Arg Tyr Pro Lys Glu Lys Phe Ile Cys Pro Asn Lys Lys Lys Asn
65                  70                  75                  80

Val Ile Thr Asp Lys Asp Ile Met Leu Ile Arg Leu Asp Arg Pro Val
                85                  90                  95

Lys Asn Ser Glu His Ile Ala Pro Leu Ser Leu Pro Ser Asn Pro Pro
            100                 105                 110
```

```
Ser Val Gly Ser Val Cys Arg Ile Met Gly Trp Gly Ala Ile Thr Thr
        115             120             125
Ser Glu Asp Thr Tyr Pro Asp Val Pro His Cys Ala Asn Ile Asn Leu
        130             135             140
Phe Asn Asn Thr Val Cys Arg Glu Ala Tyr Asn Gly Leu Pro Ala Lys
145             150             155             160
Thr Leu Cys Ala Gly Val Leu Gln Gly Gly Ile Asp Thr Cys Gly Gly
                165             170             175
Asp Ser Gly Gly Pro Leu Ile Cys Asn Gly Gln Phe Gln Gly Ile Leu
                180             185             190
Ser Trp Gly Ser Asp Pro Cys Ala Glu Pro Arg Lys Pro Ala Phe Tyr
        195             200             205
Thr Lys Val Phe Asp Tyr Leu Pro Trp Ile Gln Ser Ile Ile Ala Gly
        210             215             220
Asn Lys Thr Ala Thr Cys Pro
225             230

<210> SEQ ID NO 2
<211> LENGTH: 14
<212> TYPE: PRT
<213> ORGANISM: Bothrops atrox

<400> SEQUENCE: 2

Ile Gln Ser Ile Ile Ala Gly Asp Lys Thr Ala Thr Cys Pro
1               5                   10

<210> SEQ ID NO 3
<211> LENGTH: 8
<212> TYPE: PRT
<213> ORGANISM: Bothrops atrox

<400> SEQUENCE: 3

Gly Asp Lys Thr Ala Thr Cys Pro
1               5

<210> SEQ ID NO 4
<211> LENGTH: 14
<212> TYPE: PRT
<213> ORGANISM: Bothrops atrox

<400> SEQUENCE: 4

Val Ile Gly Gly Asp Glu Cys Asp Ile Asn Glu His Pro Phe
1               5                   10

<210> SEQ ID NO 5
<211> LENGTH: 20
<212> TYPE: PRT
<213> ORGANISM: Bothrops atrox

<400> SEQUENCE: 5

Gly Ala Ile Thr Thr Ser Glu Asp Thr Tyr Pro Asp Val Pro His Cys
1               5                   10                  15
Ala Asn Ile Asn
            20
```